(12) United States Patent
Leslie

(10) Patent No.: US 10,458,966 B2
(45) Date of Patent: Oct. 29, 2019

(54) **EGG CANDLING AND RELOCATION APPARATUS FOR USE WITH *IN OVO* INJECTION MACHINES**

(71) Applicant: BOEHRINGER INGELHEIM ANIMAL HEALTH USA INC., Duluth, GA (US)

(72) Inventor: Christopher Davis Leslie, Cleveland, GA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 15/686,234

(22) Filed: Aug. 25, 2017

(65) Prior Publication Data

US 2018/0059083 A1 Mar. 1, 2018

Related U.S. Application Data

(60) Provisional application No. 62/379,337, filed on Aug. 25, 2016.

(51) Int. Cl.
| | |
|---|---|
| *A01K 43/00* | (2006.01) |
| *G01N 33/08* | (2006.01) |
| *B07C 5/34* | (2006.01) |
| *B25J 11/00* | (2006.01) |
| *B25J 15/06* | (2006.01) |
| *G01N 21/95* | (2006.01) |

(Continued)

(52) U.S. Cl.
CPC .......... *G01N 33/085* (2013.01); *A01K 43/00* (2013.01); *A01K 45/007* (2013.01); *B07C 5/3416* (2013.01); *B25J 11/0045* (2013.01); *B25J 15/0616* (2013.01); *G01N 21/951* (2013.01); *G01N 23/06* (2013.01); *G01N 29/04* (2013.01); *B07C 2501/0081* (2013.01); *Y10S 901/02* (2013.01)

(58) Field of Classification Search
CPC .......... B07C 5/3416; B07C 2501/0081; A01K 43/00; A01K 43/04; A01K 45/007; G01N 33/08; G01N 33/0851
USPC .................................................. 209/510, 511
See application file for complete search history.

(56) References Cited

U.S. PATENT DOCUMENTS

| | | | | | |
|---|---|---|---|---|---|
| 3,437,096 | A | * | 4/1969 | Warren | B65B 23/08 134/104.3 |
| 4,302,142 | A | * | 11/1981 | Kuhl | B65B 23/08 414/416.07 |

(Continued)

FOREIGN PATENT DOCUMENTS

| | | |
|---|---|---|
| CN | 103791326 | 5/2014 |
| WO | 2002083848 A2 | 10/2002 |

(Continued)

OTHER PUBLICATIONS

Bourely et al. Robotic egg candling system. California Agriculture, Jan.-Feb. 1987.

*Primary Examiner* — Joseph C Rodriguez
(74) *Attorney, Agent, or Firm* — Judy Jarecki-Black; Steffan Finnegan

(57) ABSTRACT

The invention relates to a candling apparatus for the rapid discrimination, removal and relocation of non-live avian eggs. The invention further relates to methods of use of the candling apparatus for the candling, removal and relocation of avian eggs.

12 Claims, 20 Drawing Sheets

(51) Int. Cl.
*G01N 23/06* (2018.01)
*G01N 29/04* (2006.01)
*A01K 45/00* (2006.01)

(56) References Cited

U.S. PATENT DOCUMENTS

| | | | | |
|---|---|---|---|---|
| 4,768,919 | A * | 9/1988 | Borgman | B65G 47/91 |
| | | | | 53/495 |
| 4,805,778 | A * | 2/1989 | Nambu | A01K 43/00 |
| | | | | 209/3.3 |
| 5,017,003 | A * | 5/1991 | Keromnes | G01N 33/085 |
| | | | | 209/510 |
| 5,898,488 | A * | 4/1999 | Kuhl | A01K 43/00 |
| | | | | 356/53 |
| 6,149,375 | A * | 11/2000 | Hebrank | A01K 43/00 |
| | | | | 414/737 |
| 6,234,320 | B1 * | 5/2001 | Hebrank | A01K 43/00 |
| | | | | 209/51 |
| 6,240,877 | B1 * | 6/2001 | Bounds | A01K 43/00 |
| | | | | 119/6.8 |
| 6,750,954 | B2 * | 6/2004 | Hebrank | A01K 43/00 |
| | | | | 356/53 |
| 6,796,241 | B2 * | 9/2004 | Catalan | B41F 17/001 |
| | | | | 101/41 |
| 6,981,470 | B2 * | 1/2006 | Gross | A01K 45/007 |
| | | | | 119/322 |
| 7,083,208 | B2 | 8/2006 | Ilich | |
| 7,096,820 | B2 * | 8/2006 | Correa | A01K 45/007 |
| | | | | 119/6.8 |
| 7,878,147 | B2 * | 2/2011 | Correa | A01K 45/007 |
| | | | | 119/6.8 |
| 8,339,587 | B2 * | 12/2012 | Hebrank | A01K 45/007 |
| | | | | 356/53 |
| 8,339,588 | B2 | 12/2012 | Foster | |
| 8,610,018 | B2 * | 12/2013 | Phelps | A01K 45/00 |
| | | | | 209/511 |
| 8,696,297 | B2 * | 4/2014 | Mogenet | A01K 43/00 |
| | | | | 356/52 |
| 9,494,565 | B2 * | 11/2016 | Nambu | G01N 33/085 |
| 9,521,831 | B2 * | 12/2016 | Suh | A01K 45/007 |
| 9,839,204 | B2 * | 12/2017 | Federowicz | A01K 45/007 |
| 9,894,886 | B2 * | 2/2018 | Suh | A01K 45/00 |
| 2006/0082759 | A1 | 4/2006 | Hebrank et al. | |
| 2008/0149033 | A1 | 6/2008 | Hebrank et al. | |
| 2010/0180821 | A1 | 7/2010 | Poulard et al. | |
| 2010/0221093 | A1 | 9/2010 | Mogenet et al. | |
| 2013/0239895 | A1 * | 9/2013 | Federowicz | A01K 45/007 |
| | | | | 119/6.8 |
| 2014/0109712 | A1 | 4/2014 | Ono | |
| 2015/0293033 | A1 | 10/2015 | Tsuboi | |

FOREIGN PATENT DOCUMENTS

| | | |
|---|---|---|
| WO | 2003096028 A2 | 11/2003 |
| WO | 2009039520 A1 | 3/2009 |

\* cited by examiner

EGG CANDLING AND RELOCATION APPARATUS FOR USE WITH *IN OVO* INJECTION MACHINES

CROSS-REFERENCE TO RELATED APPLICATIONS

This application claims benefit of U.S. provisional application No. 62/379,337, filed on 25 Aug. 2016, and herein incorporated by reference in its entirety.

INCORPORATION BY REFERENCE

All references cite below are herein incorporated by reference in their entirety.

FIELD OF THE INVENTION

The invention relates to an automatic egg candling and relocation apparatus and methods of use for candling and relocation of avian eggs.

BACKGROUND OF THE INVENTION

Discrimination between live and non-live poultry eggs is a well-known in the poultry industry. "Candling" is a common name for one such technique. Eggs to be hatched are typically candled to identify clear (unfertilized), rotted, and dead eggs (collectively "non-live eggs"). Non-live eggs are removed to reduce the risk of contamination and the costs of in ovo vaccination. Automated egg removal apparatus are known (e.g. U.S. Pat. No. 7,083,208 to Embrex), but current systems tend to employ arrays of suction cups, making it impractical to place non-live eggs into a discrete location for a subsequent use (e.g. filling an egg carton for later sale of unfertilized eggs). Moreover, the poultry industry is constantly looking for improved ways of separating live and non-live eggs that are efficient, that reduce costs, and that reduce the risk of contamination to live eggs. Applicants thus sought to develop an improved automatic egg candling and relocation apparatus, which can place the non-live eggs in specific locations, including into an egg carton.

SUMMARY OF THE INVENTION

The instant invention is based upon the successful engineering of an improved egg candling and relocation apparatus that rapidly identifies, removes and relocates individual eggs from an egg carrier, including a hatchery tray. Accordingly, it is one object of the present invention is to provide an egg candling and relocation apparatus that is capable of rapid discrimination, removal and relocation of non-live eggs from a mixed plurality of live and non-live eggs. Owing to its superior discrimination capability, it is envisioned that the apparatus may also be used to select and relocate live/viable eggs.

In some embodiments, the apparatus is configured to receive an egg carrier/hatchery tray comprising a plurality of live and non-live eggs. The apparatus comprises a tray-conveying means, which is configured to move the tray along the length of the apparatus. After the tray is received into the apparatus, the conveying means moves the tray into a candling position. The apparatus comprises a candling light source, which is configured to direct light at the plurality of eggs. The apparatus also comprises a means for detecting the light that is able to pass through the eggs. In some embodiments, the detecting means is a camera, which is configured to receive the light that passed through the plurality of eggs. The camera is electrically connected to a suitable processing means, such that information about the light passing through the eggs can be processed to determine which eggs are live and which eggs are non-live.

Once the non-live eggs are determined by the processing means, this information is communicated to a robotic arm controlling means, which instructs the arm to remove the non-live eggs from the plurality of eggs. The arm comprises a suction cup, which is configured to releasably engage with the eggs, to allow the arm to pick up eggs from one location, and to drop off or place the eggs in another location. In some embodiments, the arm picks up non-live eggs from the hatchery tray and drops them off directly into a carton, for later use. Once the non-live eggs are removed, the tray is moved to an exit portion of the apparatus. In some embodiments, the apparatus is configured to reversibly attach to an in ovo injection apparatus, which comprises a plurality of injectors, and which may be configured to conditionally deliver vaccine and/or other medicaments only when an egg is present beneath one of the injectors.

Accordingly, the egg candling and relocation apparatus minimally comprises: a means for conveying hatchery trays; an egg lifting means comprising a vacuum system, for reversibly supplying suction to eggs, and a robotic arm, which is mechanically and operably connected to the vacuum system, and which is configured to reversibly apply suction to individual eggs; a light source, configured to direct light at the eggs; a vision camera, configured to receive the light that passes through the eggs; a computer, configured to process, store and communicate the information collected by the camera; and, at least one computer control, configured to direct the activities of the components of the apparatus.

In some embodiments, the egg lifting means is a robot that includes: a flexible suction cup; pneumatic circuitry, which is configured to allow air pressure to be raised and lowered inside the suction cup when the suction cup is in contact with an egg; a pedestal; a first arm connected to the pedestal and capable of swiveling around a first axis in relation to the pedestal; a second arm connected to the first arm and capable of swiveling around a second axis that is parallel to the first axis and spaced apart from the first axis, in relation to the first arm; and a wiring section which accommodates a wire therein and conveys the wire from the second arm to the pedestal. The wiring section includes: a duct supporting portion provided to protrude from the pedestal and intersect with the first axis; a first joint connected to the duct supporting portion and capable of swiveling around the first axis in relation to the duct supporting portion; a second joint connected to the second arm and capable of swiveling around the second axis in relation to the second arm; and a duct connected to the first joint and the second joint. The first joint is provided with a first connecting portion forming a predetermined angle relative to the first axis. The second joint is provided with a second connecting portion forming a predetermined angle relative to the second axis. The duct has a first end and a second end. The first end is connected to the first connecting portion. The second end is connected to the second connecting portion. In general, any suitable robotic arm may be used in the practice of this invention, for example, the robotic arm described in US 2014/0109712A1 (to Epson), which is herein incorporated by reference in its entirety.

In some embodiments, the egg lifting robot includes a vacuum generator having first and second passageways, in fluid communication with the first and second passageways, and a flexible cup positioned at a terminal end of a robotic egg-lifting arm, wherein the flexible cup comprises an interior that is in fluid communication with the vacuum generator second passageway. The vacuum generator produces subatmospheric pressure (vacuum) within the second passageway upon actuation of a vacuum generator pneumatic control valve. The control valve may be actuated by any suitable actuator, including an electrical, pneumatic or hydraulic actuator. The flexible cup is configured to engage and retain an egg in seated relation therewith when subatmospheric pressure is provided within the flexible cup interior via the vacuum generator second passageway.

In some embodiments, the flexible cup is removably secured to a suction cup mount, which is operably connected to a vertical quill of the robotic arm. A screen may be positioned within the interior of the flexible cup and may be configured to prevent foreign matter from being pulled into the passageway of the vacuum generator.

In some embodiments, an apparatus for removing eggs from an egg carrier (e.g. a hatchery tray) includes a frame, a pressurized air source, and a platform comprising at least one robotic arm egg lifting apparatus.

In some embodiments, a method of cleaning and/or sterilizing the egg lifting apparatus includes immersing the flexible cup in a bath of cleaning solution, and inducing vacuum within the interior of the vacuum cup by forcing air flow through the vacuum housing first passageway, wherein contaminants are pulled upwardly through the second passageway and out assembly.

In some embodiments, the egg-relocation apparatus is adaptable to in ovo injection machines, for example, but not limited to INTELLIJECT® and OVOJECTOR®. In still other embodiments, the egg-relocation apparatus may comprise and additional egg-lifting robot, which may be configured to fill empty spaces in an egg carrier with viable eggs. In such an embodiment, there the subsequent in ovo injection machine need not be configured to deliver vaccine or other fluids only when an egg is present, since the entire egg carrier will be populated with viable eggs, ready for injection.

In some embodiments, the egg-candling and relocation apparatus may remove clear eggs from a production line before vaccination at any time between day 17+12 hours and day 19+12 hours of incubation. "Clear" eggs are defined herein as entirely infertile, early dead (gestation cessation at day 1-5) and most early-mid dead (gestation cessation at day 6-11); non-clear eggs are defined herein as late-mid dead (gestation cessation at day 11-14), late dead (gestation cessation at day 15-transfer), contaminated and live. In ideal embodiments, the egg-candling and relocation apparatus is capable of discriminating among infertile, early dead, most early-mid dead, late-mid dead, late dead, contaminated and live; and, the apparatus is capable of relocating all non-live/non-viable eggs. In this way, only live/viable eggs will remain in the egg carrier, to be presented to a suitable in ovo injection machine for subsequent injection.

In a particular embodiment, the apparatus is at least 99.9% accurate in identifying and relocating clear eggs, and is 100% accurate in not relocating viable eggs. Clear eggs remain intact during removal and may be automatically relocated into egg cartons for resale.

Accordingly, it is an object of the invention to not encompass within the invention any previously known product, process of making the product, or method of using the product such that Applicant reserves the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (51 U.S.C. § 112, first paragraph) or the EPO (Article 83 of the EPC), such that Applicant reserves the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may be best understood in conjunction with the accompanying drawings, in which.

DETAILED DESCRIPTION

Figure 1:
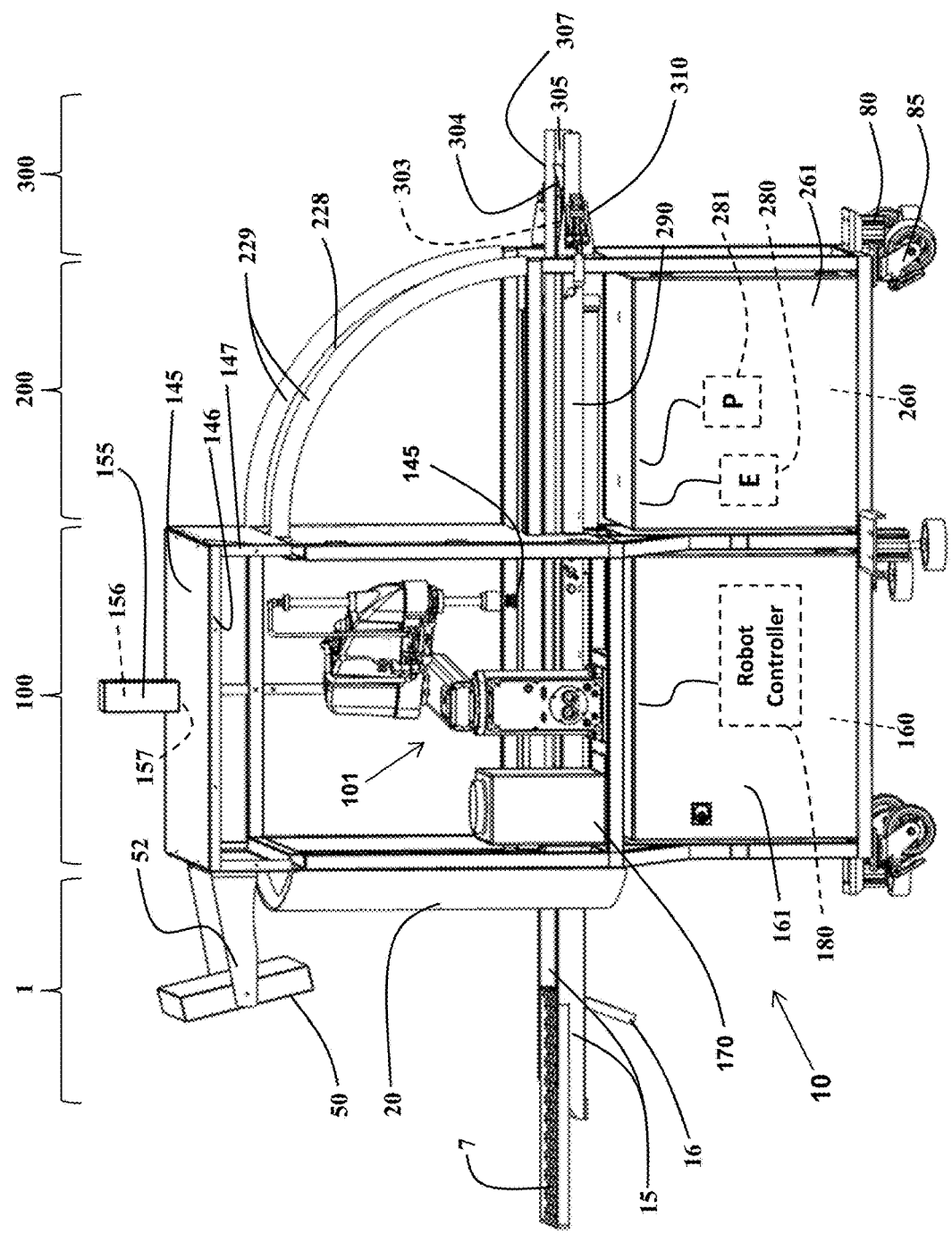
FIG. 1 is a side view of an egg candling and relocation apparatus, according to embodiments of the present invention.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise. Finally, "about" has the ordinary meaning of "plus or minus 10%."

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

All publications, patent applications, patents, and other references mentioned herein are incorporated by reference in their entirety.

In the drawings, the thickness of lines, layers and regions may be exaggerated for clarity. It will be understood that when an element is referred to as being "on" another element, it can be directly on the other element or intervening elements may also be present. In contrast, when an element is referred to as being "directly on" another element, there are no intervening elements present. It will be understood that when an element is referred to as being "connected" or "attached" to another element, it can be directly connected or attached to the other element or intervening elements may also be present. In contrast, when an element is referred to as being "directly connected" or "directly attached" to another element, there are no intervening elements present. The terms "upwardly", "downwardly", "vertical", "horizontal" and the like are used herein for the purpose of explanation only. In one aspect, the present invention provides Egg candling and relocation apparatus according to embodiments of the present invention may be utilized for distinguishing and relocating various types and sizes of eggs (e.g. live/viable, clear, unfertilized, dead, and the like) and in conjunction with various egg processing techniques (e.g., in ovo inoculation/injection, in ovo virus cultivations, etc.). Egg candling and relocation apparatus according to embodiments of the present invention may be used with any type of avian eggs including, but not limited to, chicken eggs, turkey eggs, duck eggs, geese eggs, quail eggs, pheasant eggs, exotic bird eggs, etc.

Referring now to FIGS. 1-10, an egg candling and relocation apparatus 10, according to embodiments of the present invention is illustrated. The illustrated candling and relocation apparatus 10 includes a set of outer loading rails 15, configured to receive an egg carrier 7 (e.g. hatchery tray) into a loading area 1. The outer rails 15, inner rails 17 and support member 16 collectively form a table or shelf, which may be collapsible to facilitate transportation of the apparatus. The support member 16 is configured to reversibly attach to a support member rod 18 (not shown), which supports the table in its horizontal or non-collapsed position. After entering the apparatus at the loading area 1, the egg carriers 7 are conveyed into the candling station 100, where non-viable eggs are removed and relocated, and then, the remaining viable eggs are transported to the viable egg staging station 200. Finally, the eggs are conveyed out of the apparatus, and, ideally, directly into a compatible in ovo injection machine.

Affixed near or adjacent to loading area 1 is a user interface touch screen 50, which is mounted to the apparatus via mounting means 52. The screen 50 is electrically connected to, and is capable of controlling, all the mechanical and electrical functions of the apparatus 10.

Atop the apparatus 10 is a camera enclosure 55, for housing a camera 56, which is configured to receive light that passes through a plurality of eggs 5, which are contained within an egg carrier/hatchery tray 7. Light captured by the camera is converted therein into digital information, which is accessible by a processor or controller that controls the motion of an egg relocation apparatus 101. Various panels provide containment and protection for the eggs as they are conveyed through the apparatus 10, including: an entrance panel 20; a candling station top panel 145; onto which the camera enclosure 155 is mounted, and comprising an orifice 157 through which the light or the camera 156 may pass; and, a viable egg staging area 200 top panel 228. Panel 145 is affixed to and supported by horizontal frame members 146 and vertical frame members 147. Similarly, panel 228 is affixed to and supported by curved frame members 229. Other panels are presented in subsequent Figures, and all of the panels and supportive structures may be routinely modified (e.g. opaque materials may be exchanged for transparent or translucent materials; metallic materials may be exchanged for composite/synthetic materials).

Within the space immediately above the robot controller 180 cabinet door 160, a sanitation fluid tank 170 and an egg relocation robot 101 are mounted to horizontal portions of the frame of the apparatus. The robot 101 must be situated such that it can lift and relocate any of a plurality of eggs 5 contained within an egg carrier 7, while still being able to extend the flexible egg-relocation cup 145 into the sanitation tank 170 for cleaning. Alternatively, the robot could be suspended from above instead of mounted as shown in FIG. 1. To the right of the robot controller cabinet 160 is a cabinet 260, which house an electrical controller 280 and a pneumatic controller 281. Appropriate conduits and electrical connectivity are included to allow a user to control all aspects of the apparatus using interface 50.

An egg carrier 7 is shown entering the "loading table," via rails 15. The carrier will next be guided to the candling area 100, then to the viable egg staging area 200, and finally to an exit area 300. From the exit area 300, the carrier 7 will be conveyed or transferred to a compatible in ovo injection machine 400. An egg carrier transfer component/carriage 303 (equipped with clasping means 304, 306) and apparatus joining means 305 are configured to allow the egg candling and relocation apparatus 10 to reversibly connect to a compatible in ovo injection machine 400. Securing means 310 are configured to allow the apparatus 10 to be reversibly locked or secured to the in ovo injection machine 400. Finally, the apparatus 10 is configured such that it is portable, yet stable once it has been moved into the desired position. Lockable casters 80 and braking means 85 provide the apparatus with these necessary portability and stability functionality.

Figure 2:
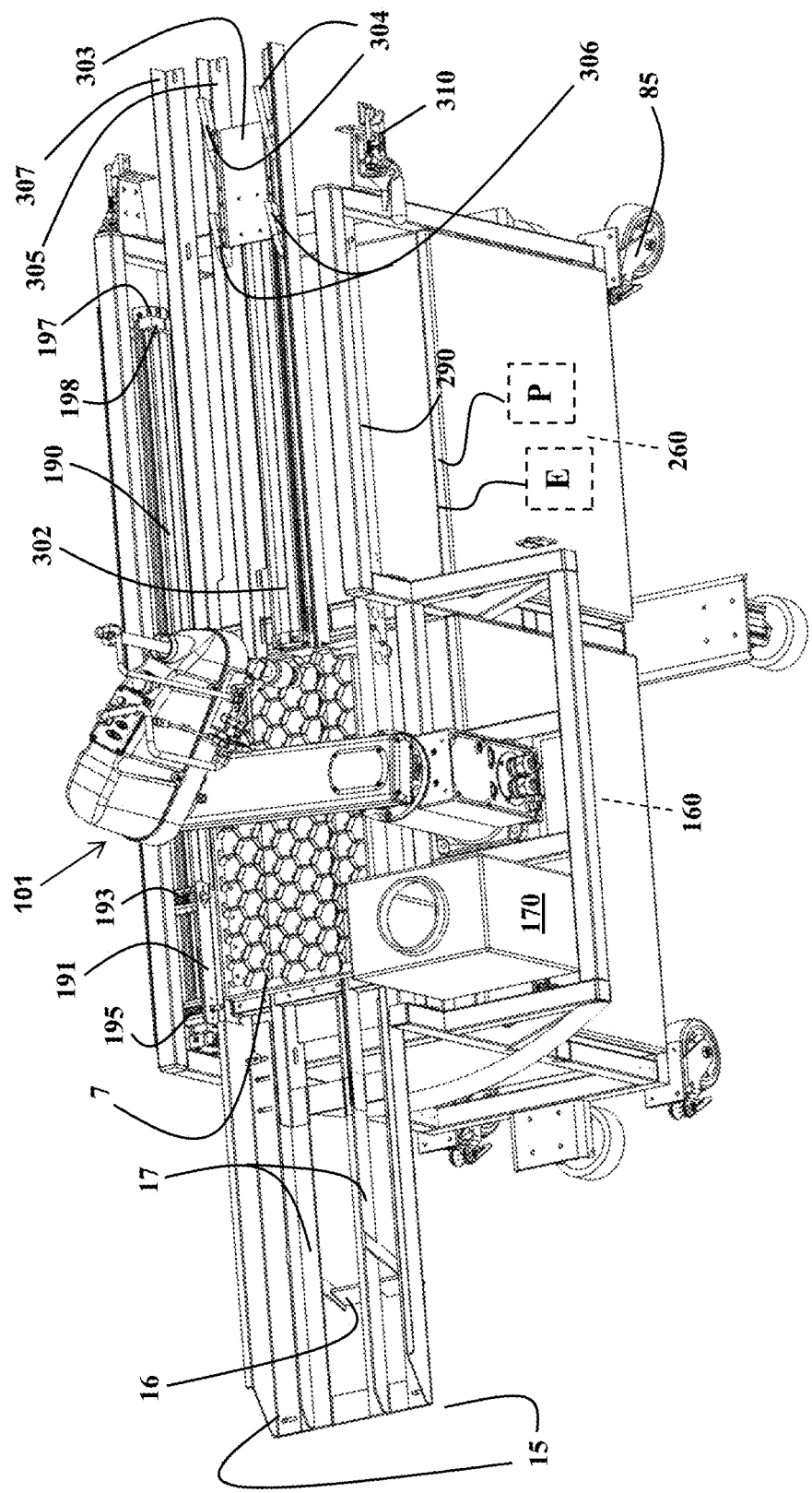
FIG. 2 is an internal and elevated view of the apparatus of FIG. 1 that illustrates the various components thereof.

Turning now to FIG. 2, which shows an internal and elevated view of the apparatus of FIG. 1, with its top enclosure and frame portions removed. The external rails 15, along with the internal rails 17, form a table or shelf, which may be collapsible from its depicted horizontal position to a vertical storage/transportation position. In the case where the table or shelf is collapsible, the support member 16 is configured to reversibly attach to a support member rod 18 (not shown), which may be pivotably affixed to the frame of the egg candling area 200, such that the rod 18 can extend to connect to a support the table. With the top enclosure and frame portions removed, an egg flat/carrier 7 is shown adjacent to an egg flat/tray carriage 191, which is configured to reversibly engage with and move the egg flat 7 from the egg candling area 100 to the viable egg staging area 200.

As indicated in FIG. 2, the egg flat carriage 191 comprises 2 orifices through with air cylinder 195 and air cylinder 193 extend. Air cylinders 195 and 193 are operably connected to a front transfer cylinder 190, such that when the transfer cylinder 109 is actuated by pneumatic force, cylinders 195 and 193 are moved laterally. When actuated, cylinder 195 engages with the flat, such that when cylinder 195 is moved laterally, so too does the flat. As such, cylinder 195 functions like a retractable hook, such that when extended behind the egg flat, cylinder 190 is then actuated, and the egg flat is pulled along the track. Cylinder 193 is only actuated while the robot is pulling out the identified eggs, such that cylinder 193 secures the flat so that the removal of the eggs does not move the flat and eggs out of position, relative to when the eggs to be removed were identified. When the last egg to be removed has been pulled out by the robot and suction cup, cylinder 193 retracts to allow the egg flat to be pulled along the track by the action of cylinder 195. Accordingly, in this embodiment, the sole purpose of cylinder 193 is to grip/push the flat against the side rail during the egg removal, so that the flat 7 does not move during this step. If the flat were to move, the eggs could be moved out of position, relative to the positions determined during the candling step, and the robot controller would no longer have the proper coordinate of the eggs to be removed.

During typical operation of the apparatus, a user loads a flat 7 carrying a plurality of eggs onto the shelf formed by rails 15 and 17. Once the flat 7 is moved sufficiently far enough into the egg candling area 100, the gripper cylinder 193 is actuated, and reversibly engages with the flat 7. The carriage 191 then moves along the length of the cylinder 190, thereby moving the flat 7 from the egg candling area 100 to the viable egg staging area 200. Once the tray is placed in the staging area 200, the gripper cylinder 193 disengages from the flat 7, allowing the carriage to return to its starting position at the beginning or entrance of the egg candling area 100, ready to engage with the next incoming flat 7. In this manner, egg flats 7 are serially fed into the apparatus at the far left end of the rails 15, pushed into the egg candling area 100, picked up by the carriage 191 and gripper cylinder 193, and then moved by cylinder 190 into the viable egg staging area 200.

Once the flat 7 is in the viable egg staging area 200, the carriage 303 is moved along the cylinder 302, and underneath the flat, to the end of the flat closest to the egg candling area 100 from which the flat 7 just arrived. While the carriage 302 is moving underneath the flat 7, the carriage fingers 304, 306, which are pivotably connected to the carriage 302, pivot downward as a result of making physical contact with the egg flat 7. In other words, the fingers 304, 306 are pressed down by the flat 7 as they slide beneath it. The fingers are thus configured to pivotably retract when they move beneath the egg flat 7, and configured to return to their initial positions after they clear the underside of the flat 7. In a particular embodiment, the carriage 302 moves underneath the flat 7 until the first set of fingers 306 clears the underside of the flat and returns to its initial position. The carriage 302 then reverses its direction of lateral movement, such that the fingers 306 engage with the flat 7 and move the flat from the viable egg staging area 100 toward the exit of the apparatus (i.e. toward the awaiting in ovo injection machine 400). Once the carriage reaches its ending point along cylinder 302 (e.g. as shown in FIG. 2), the carriage 302 reverses direction once more, bringing the second set of fingers 304 out from underneath the flat 7, where now all four (4) fingers 304, 306 are in their extended (i.e. initial or resting) positions. At this point, the cylinder 302 will move the carriage 303, which in turn moves the front fingers 304 to engage with the flat 7. The carriage 303 then moves into the position shown in FIG. 2, which moves the flat 7 to the end of the apparatus 10 (as shown in FIG. 3), and either off the apparatus, or onto a waiting second apparatus, for example, the in ovo injection machine 400 shown in FIG. 8.

Figure 3:
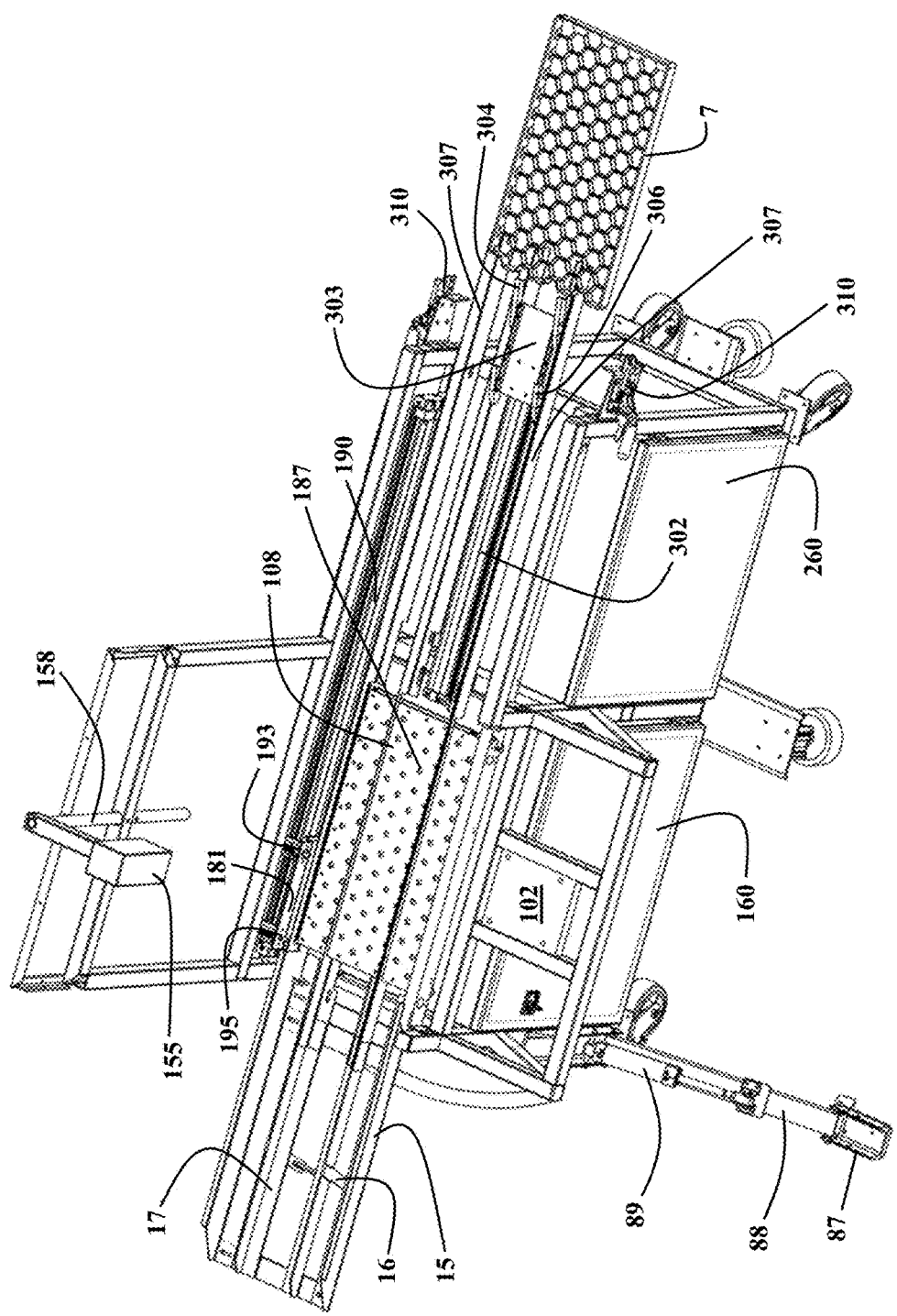
FIG. 3 is an internal and elevated view of the apparatus of FIG. 1 with the egg relocation robot removed.

FIG. 3 is an internal and elevated view of the apparatus of FIG. 1 with the egg relocation robot removed, and the egg flat 7 shown at its most distal position, ready to be transferred off the apparatus and on to an awaiting secondary apparatus. With the enclosure and upper frame portions removed, a candling light shroud 108 having a plurality of orifices 187 may be visualized. In the embodiment shown in FIGS. 1 to 10, the apparatus 10 comprises a candling light source positioned beneath the shroud 108 and configured to shine light at the shroud 108 and through the plurality of orifices 187. Applicants found surprisingly that candling fidelity/accuracy could be significantly improve by guiding the candling light through the orifices. Necessarily, the holes 187 are configured to align with the positions of the plurality of eggs held within the tray/flat 7. Also shown in FIG. 3 is a stabilizing member 88 having a foot portion 87 and a retractable pneumatic cylinder 89 configured to allow for extension and retraction of the support 88. Any suitable such supporting means may be used in the practice of the invention. Finally, a robotic arm support 102 can be seen from this view, as well as the egg tray 7 and egg tray carriage 303, which are shown at their most distal positions along the apparatus 10. In this position, the tray 7 must be supported by some downstream apparatus, for example, the in ovo injection machine shown in FIG. 8. Both the candling and relocation apparatus 10 and any downstream apparatus must be configured to reversibly connect to one another (see e.g. FIGS. 5 to 8)

Figure 4:
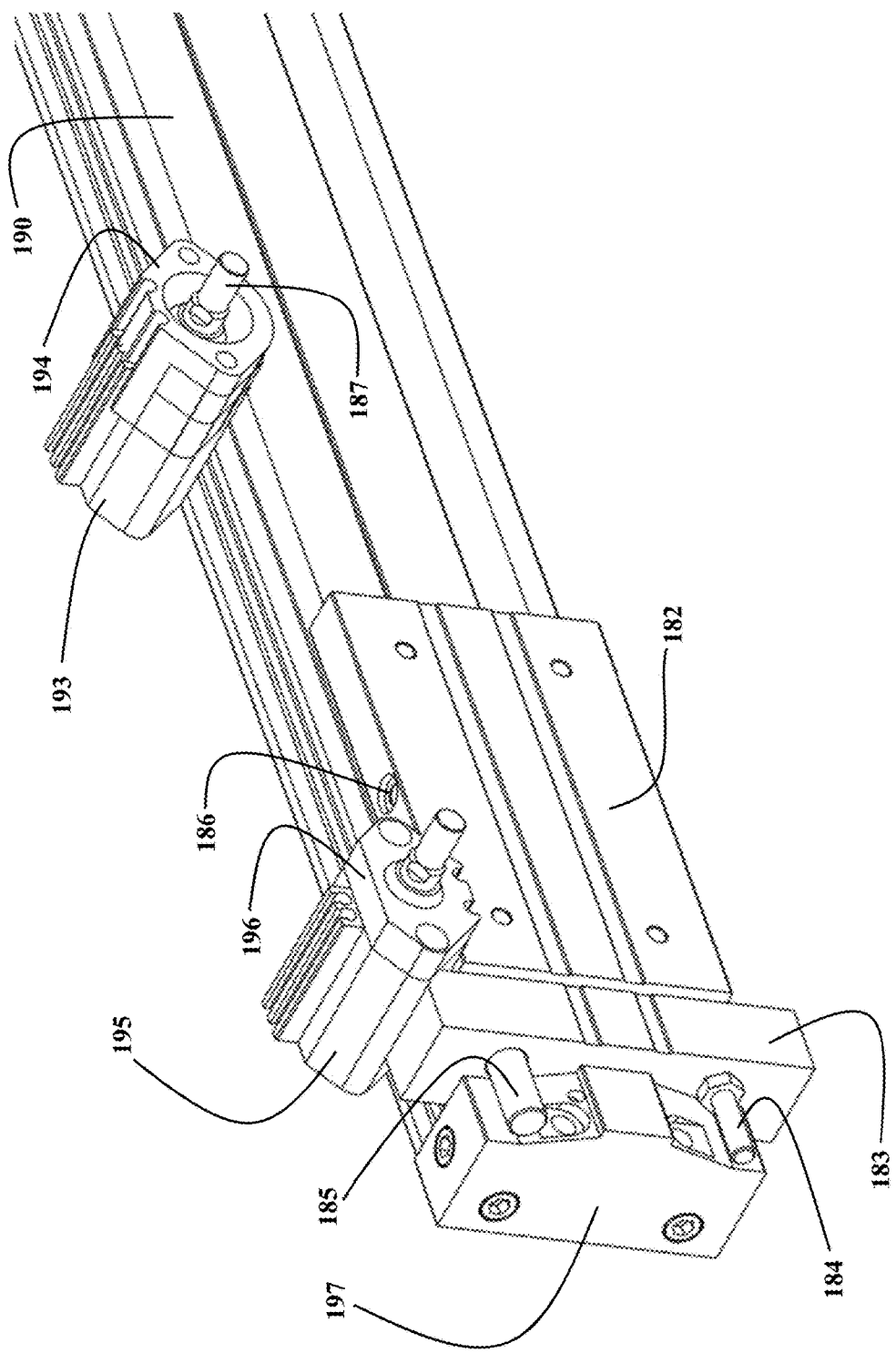
FIG. 4 is a detailed view of the actuators and track that are configured to convey egg carriers along the length of the apparatus of FIG. 1, from its loading area to its egg candling station.

FIG. 4 shows a close-up view of the pneumatic cylinder 190, which is configured to move a carriage table 182 laterally from a starting/proximal position to an ending/distal position. An egg flat carriage 181 (shown in FIG. 3) operably connects egg flat carrier cylinder 195 to egg flat gripper cylinder 193. Cylinders 195 and 193 may have different sized mounting spacers 196, 194, respectively, and gripper rod 187 is configured to extend to engage with and "grip" the egg tray 7, at the same time the robot picks and relocates the eggs. As indicated in this embodiment, a hardware mounting orifice 186 may be present atop the carriage table 182. Cylinder 190 is attached to the apparatus via cylinder end cap 197 (i.e. the mounting point for the rodless cylinder 190), and adjustable stroke limiter block 183, 198 may be placed at any point along cylinder 190 to meet a variety of range of motion requirements. Shock absorber 185 (e.g. an air or hydraulic cushion) is configured to reduce impact when base 182 moves to is proximal- or distal-most position (i.e. when the stroke limiter block strikes the mounting end cap 197), and an adjustable hard stop 184 is configured to provide an absolute hard stop location for the limiter block 183. The adjustability and shock absorbing features allow the apparatus 10 to be configured to suit a variety of conditions, including, but not limited to, different sized egg flats 7. Further, the apparatus 10 comprises suitable pneumatic and electrical connectivity to allow a user to control all aspects of the apparatus, including those of cylinders 190, 195 and 193. And finally, electrical and pneumatic features of the apparatus are controllable via user interface 50.

Figure 5:
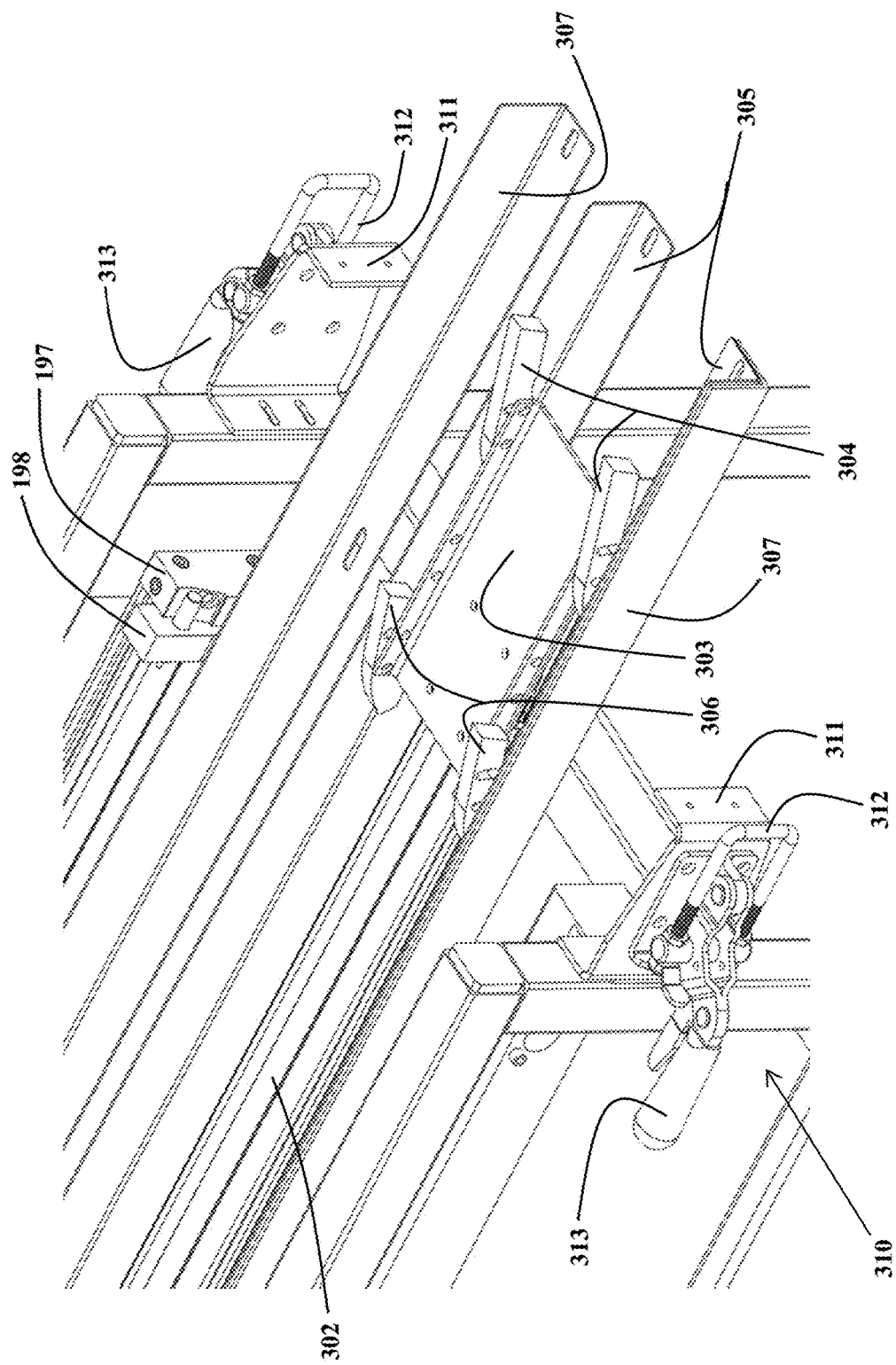
FIG. 5 is detailed view of the carriage that conveys the egg carrier from the viable egg staging area to the exit of the apparatus of FIG. 1. The apparatus is configured to be reversibly connectable to a subsequent and compatible in ovo injection apparatus, as depicted in FIGS. 7 to 8.
Figure 7:
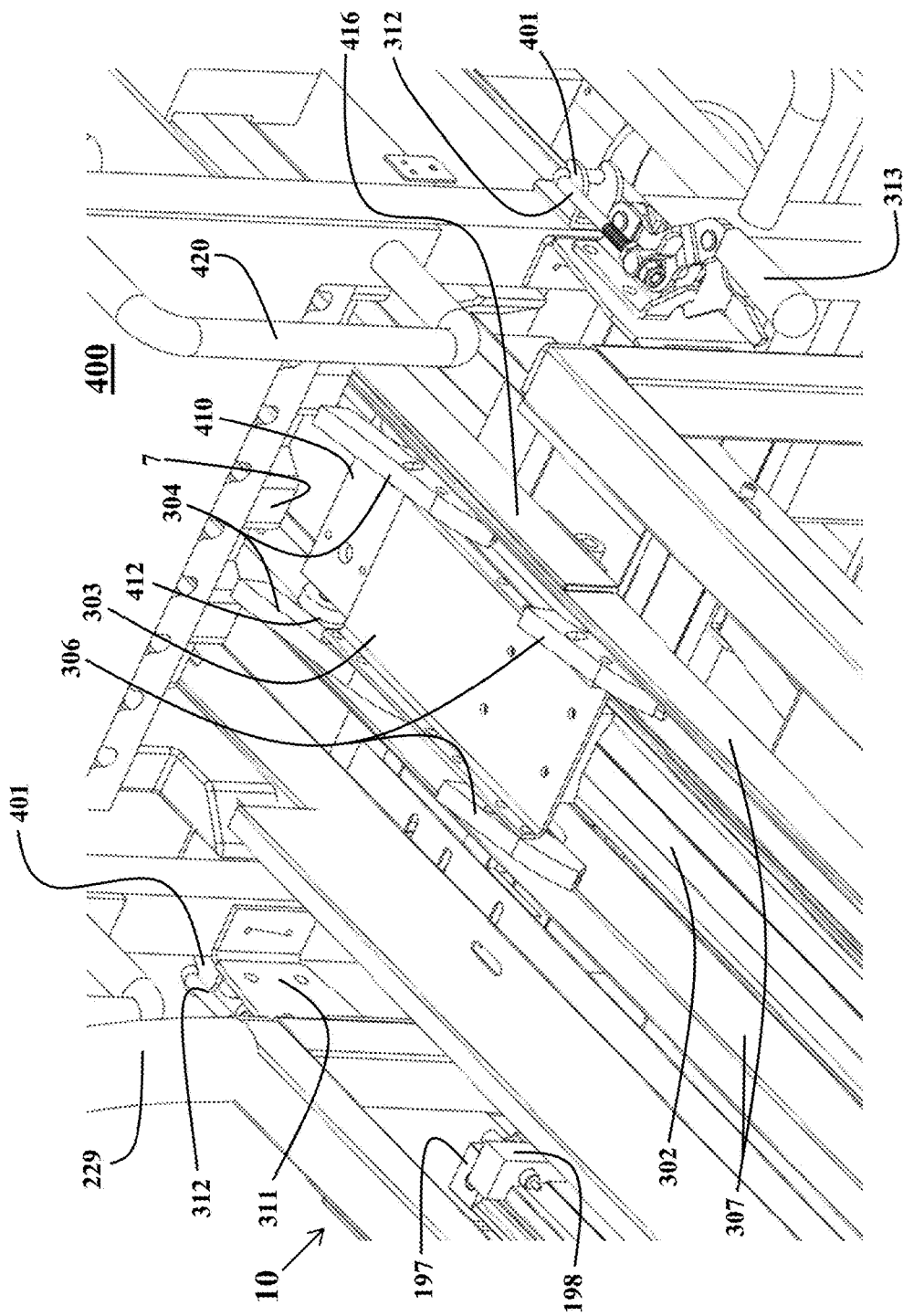
FIG. 7 is a detailed view of the apparatus of FIG. 1 connected to a compatible in ovo injection machine.
Figure 8:
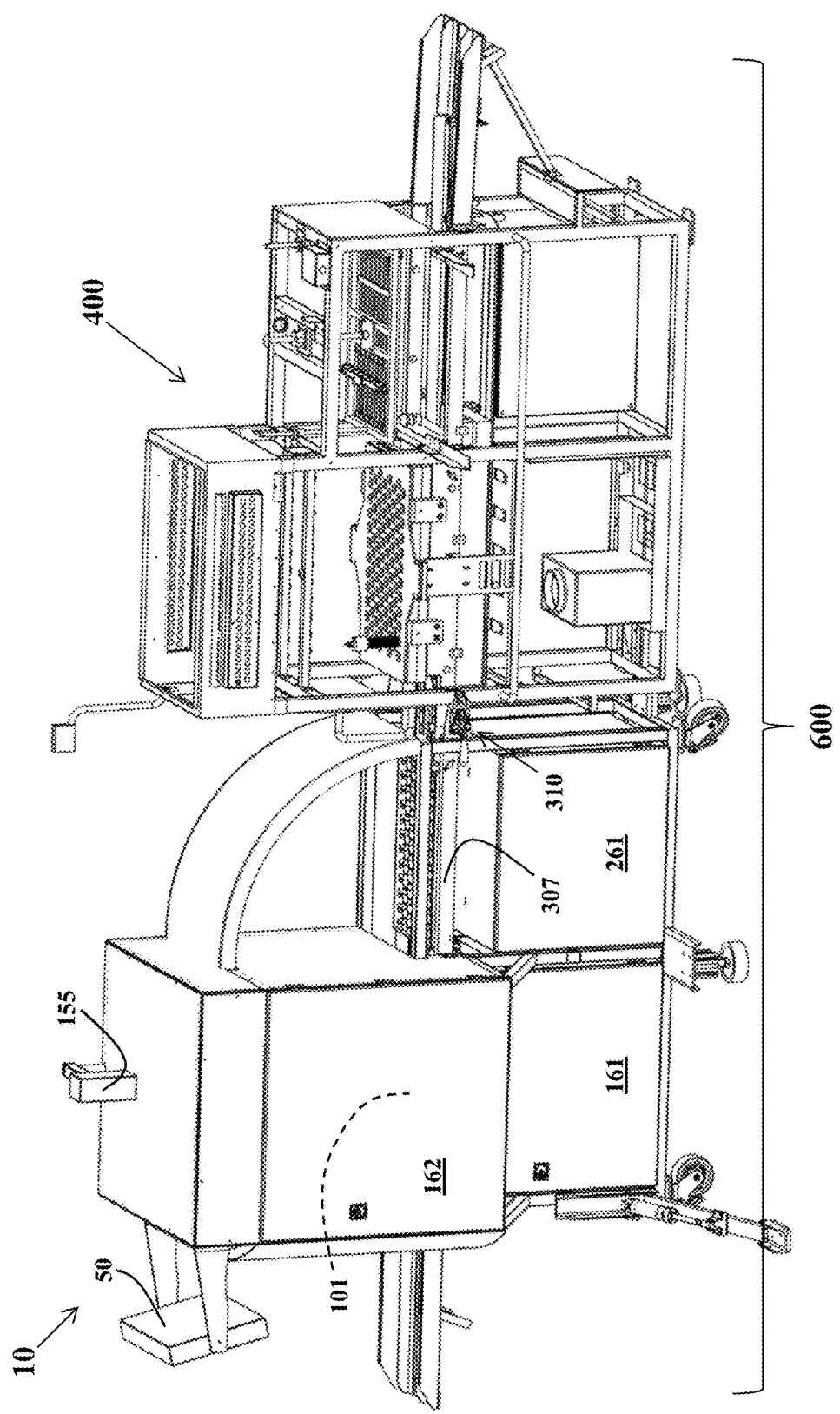
FIG. 8 is a side view of the apparatus of FIG. 1 connected to a compatible in ovo injection machine.

FIG. 5 is detailed view of the apparatus 10 new the carriage 303 and its pivotably retractable fingers 304, 306, which convey the egg carrier laterally along the rodless cylinder 302, from the viable egg staging area 200 to the exit of the apparatus of FIG. 1. The apparatus is configured to be reversibly connectable to a subsequent and compatible in ovo injection apparatus 400, as depicted in FIGS. 7 to 8. Carriage rails 305 and outer rail 307 form a table or support for the egg tray/flat 7, similarly to the way rails 15 and 17 formed a table at the entrance of the apparatus 10. The rails 305 and 307 are configured to match up with corresponding partner pieces on the downstream in ovo injection machine 400. Likewise, carriage 303 is configured to be compatible with downstream in ovo injection machine components, such that the egg tray 7 may be safely and efficiently handed off from the candling and removal apparatus 10 to the in ovo injection machine 400. Inter-apparatus connecting means 310 (e.g. draw latches, pull latches, and the like) are mounted onto mounting means 311 (e.g. brackets, braces, flanges, or the like), which themselves are mounted onto the frame of the apparatus 10. As shown, each draw latch 310 includes a handle 313 and a hook 312. The hook connects to corresponding hook receiver 401 (see FIG. 6), which is mounted onto the frame of the in ovo injection machine 400.

Figure 6:
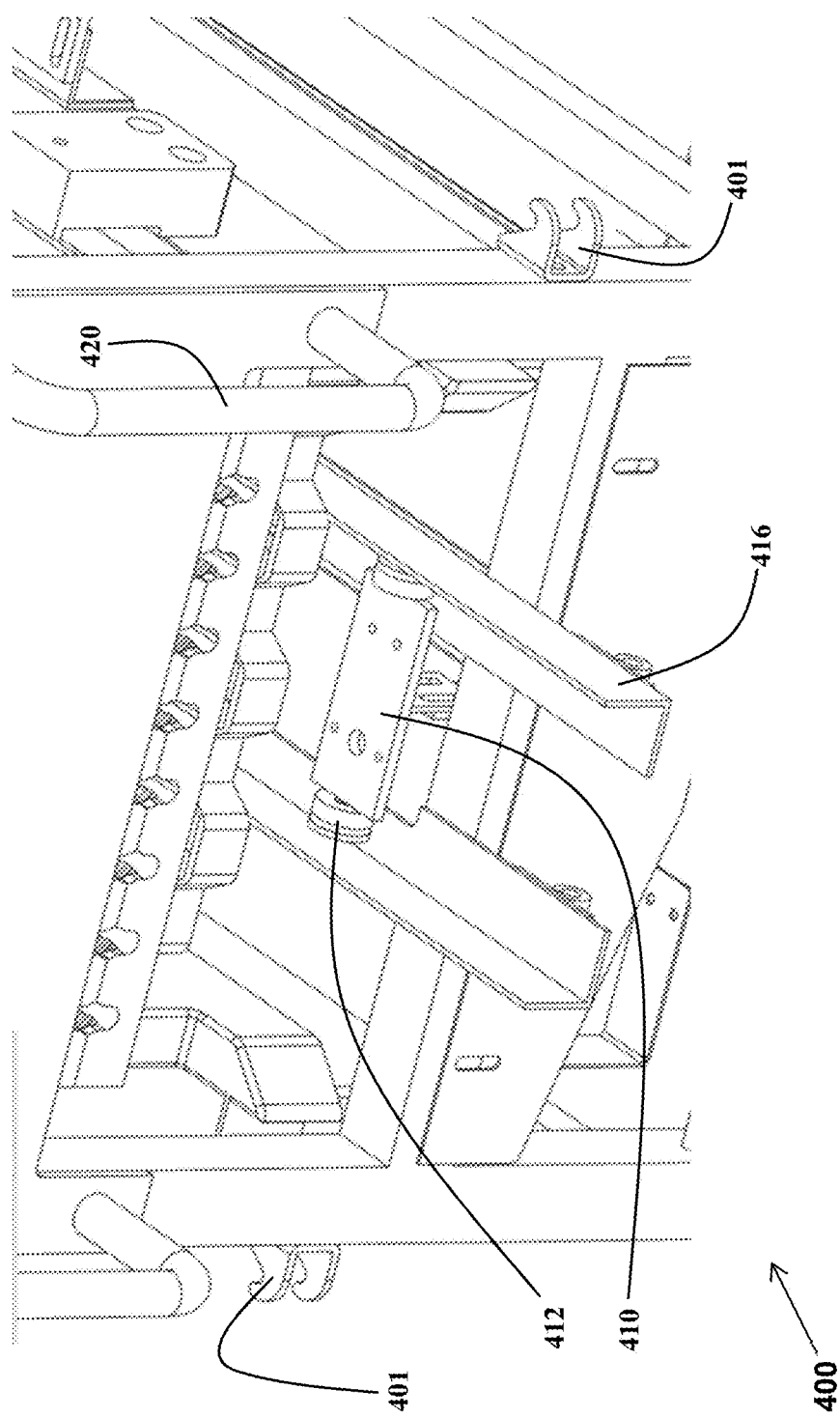
FIG. 6 is a detailed view of a compatible in ovo injection machine, which is configured to reversibly connect to the egg candling and relocation apparatus of FIG. 1.

FIG. 6 shows the in ovo injection machine 400 components that are configured to receive and/or connect with corresponding candling and removal apparatus 10 components. Shown are the handles 420, which are used to move the in ovo injection machine; and hook receivers 401, which are configured to receive and reversibly attach to the hooks 312 from the candling and removal apparatus 10. Carriage receiving rails 416 are configured to align with apparatus rails 305, such that the candling apparatus carriage 303 may be moved all the way up to in ovo machine carriage 410, which comprises wheels 412.

FIG. 7 shows the meeting and/or connection of corresponding components when the apparatus 10 is connected to the in ovo injection machine 400. The connecting means 310 and hook receivers 401 are sufficient to keep the apparatuses physically connected to one another, and the corresponding components are configured to allow and facilitate the hand off or exchange of the egg tray 7 from the apparatus 10 to the in ovo machine 400. In FIG. 7, the carriage 303 is shown at its distal-most position, having pushed the egg tray/flat 7 into the entrance of the in ovo injection machine 400. Carriage 410, which may be similarly equipped with pusher fingers (i.e. like the carriage 303), is configured to move the egg tray 7 from the beginning portion of the in ovo machine and onto subsequent portions of the machine. Finally, FIG. 8 shows the egg candling and relocation apparatus 10 connected the in ovo injection machine 400, collectively referred to herein as an egg candling, relocation and injection system 600. In a particular embodiment, the in ovo injection machine 400 is as described in U.S. Pat. Nos. 7,430,987, 7,721,674, or U.S. Pat. No. 8,201,518, each to David Smith (Profilax).

FIGS. 9A to 9E, and 10 provide details of the egg candling and relocation robotic arm 101. An example robotic arm is described in US 2014/0109712 ("the '712 publication"), to Epson. As further detailed in the Epson publication, the robot 101 is a horizontal multi joint robot. A pedestal 110 is fixed to a robot arm support 102, with bolts or the like. The first arm 120 is connected to an upper end of the pedestal 110. The first arm 120 is capable of swiveling around a first axis A1 that extends along a vertical direction, in relation to the pedestal 110. Inside the pedestal 110, a first motor 111 which causes the first arm 120 to swivel, and a first decelerator 112 are installed. An input axis of the first decelerator 112 is connected to a rotation axis of the first motor 111. An output axis of the first decelerator 112 is connected to the first arm 120. Therefore, when the first motor 111 is driven and a driving force thereof is transmitted to the first arm 120 via the first decelerator 112, the first arm 120 swivels within a horizontal plane around the first axis A1 in relation to the pedestal 110. The first motor 111 is provided with a first encoder 113 which outputs a pulse signal corresponding to the amount of rotation of the first motor 111. Based on the pulse signal from the first encoder 113, driving (amount of swiveling) of the first arm 120 in relation to the pedestal 110 can be detected. The second arm 130 is connected to a distal end of the first arm 120. The second arm 130 is capable of swiveling around a second axis A2 that extends along a vertical direction, in relation to the first arm 120. Other details of this robot, or other functionally equivalent robots, are readily available to the skilled person, for example, in product literature from robot manufacturers.

Figure 9A:
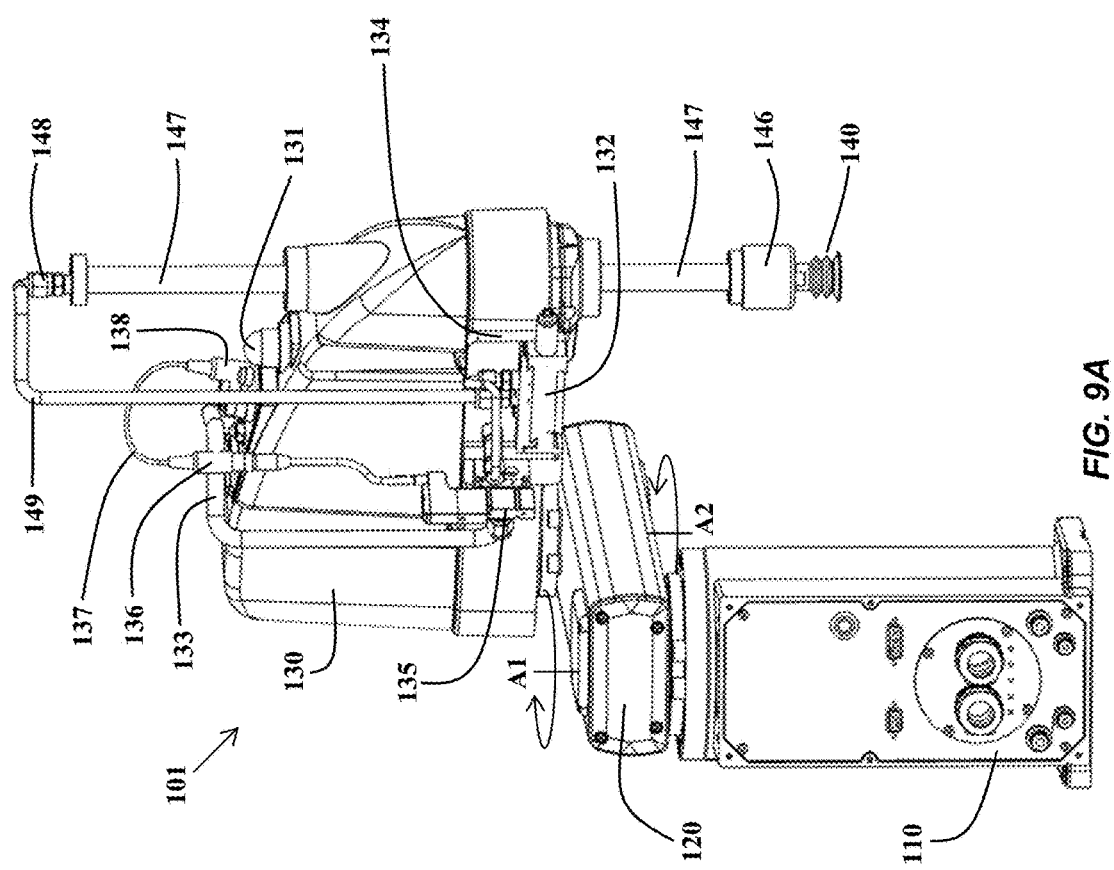
FIG. 9A is a side view of a robotic egg relocation apparatus, according to embodiments of the present invention.
Figure 9B:
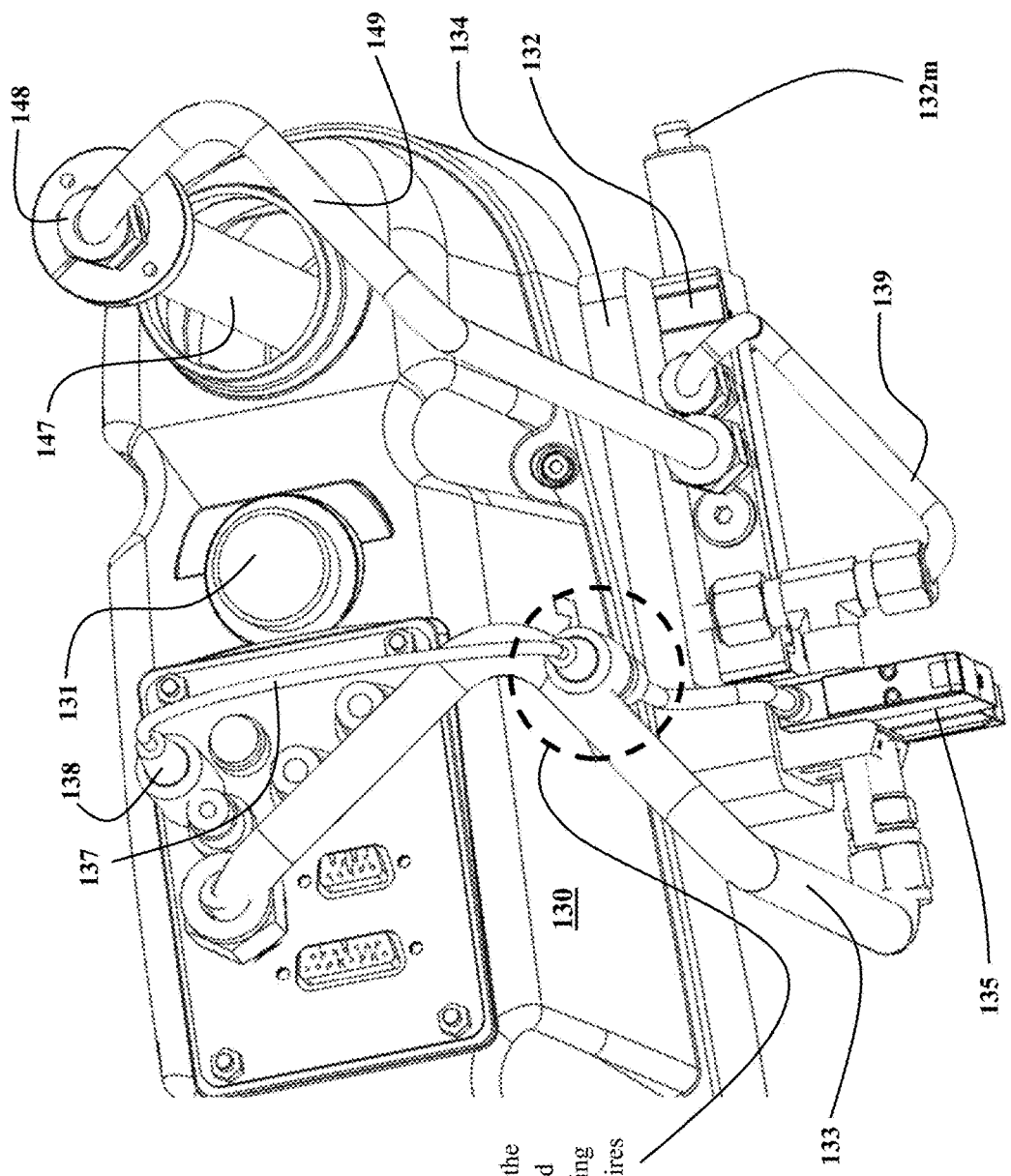
FIG. 9B is a detailed top view of the egg relocation apparatus of FIG. 9A.
Figure 9C:
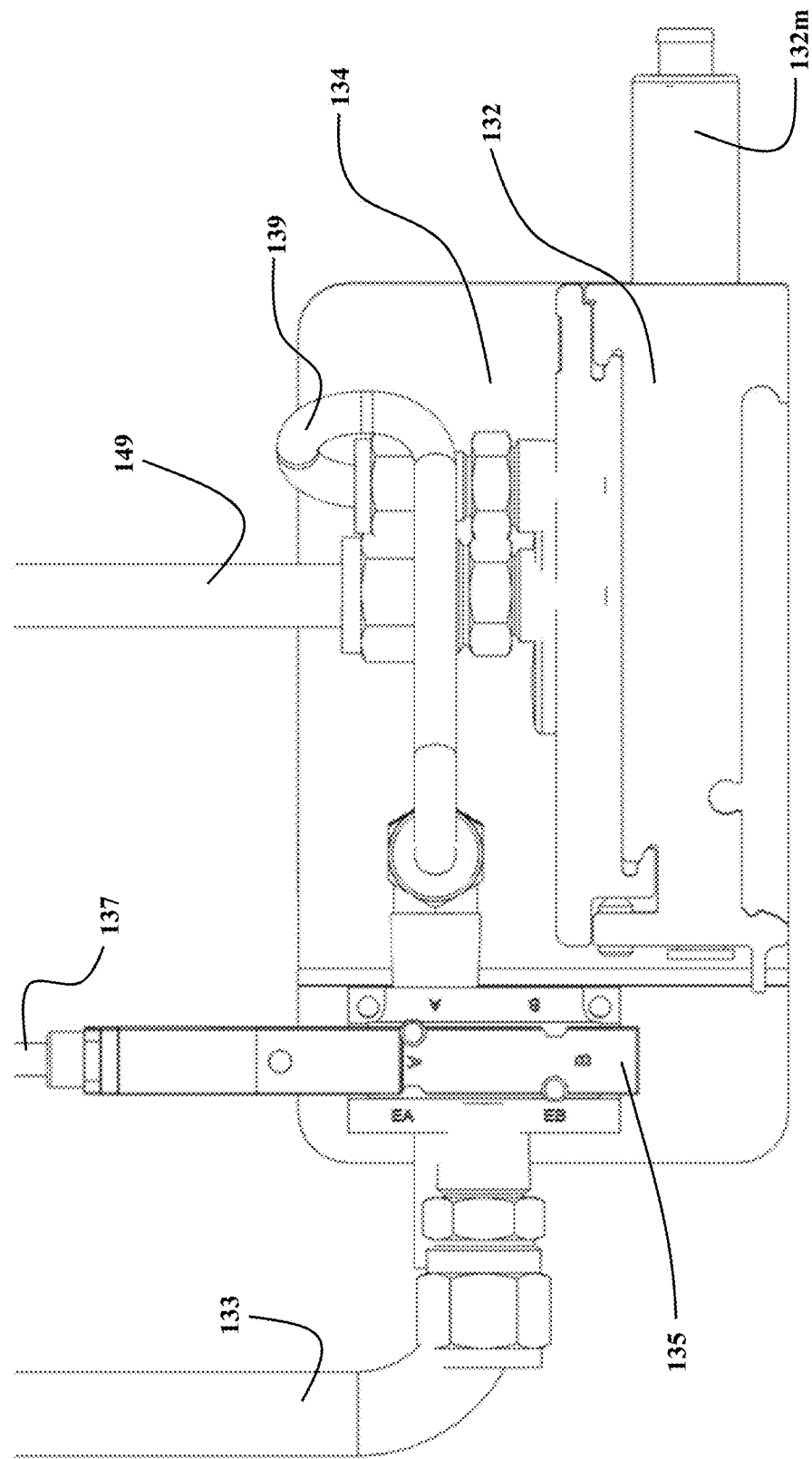
FIG. 9C is a detailed side view of the egg relocation apparatus of FIG. 9B, showing the vacuum generator and the electrical and pneumatic circuitry.

As shown in FIG. 9A, the robotic arm 101 is fitted with a variety of pneumatic and electrical circuitry, which allows the arm 101 to pick up and relocate eggs. The arm 101 of the egg candling and relocation apparatus 10 comprises flexible/elastomeric cup 140, which is configured to pick up and release spherical and ovoid objects, including avian eggs. The cup 140 is connected to a hollow shaft 147 by cup mount 146. The robotic arm 101 is configured to move the shaft 147 vertically, up and down, allowing the cup to come into contact with eggs, pick them up, and move the eggs to a selected location. Any suitable length and type of shaft 147 may be used in the practice of the invention, provided that the shaft 147 is hollow and configured to serve as a conduit for air, such that the cup 140 can be reversibly presented with subatmospheric pressure. It is this subatmospheric pressure that allows the flexible cup 140 to pick up the round and ovoid objects. The user interface 50 allows a user to control the robot controller 180, which controller is electrically connected to the robot 101, and configured to control all aspects of the robot's functions.

Figure 9D:
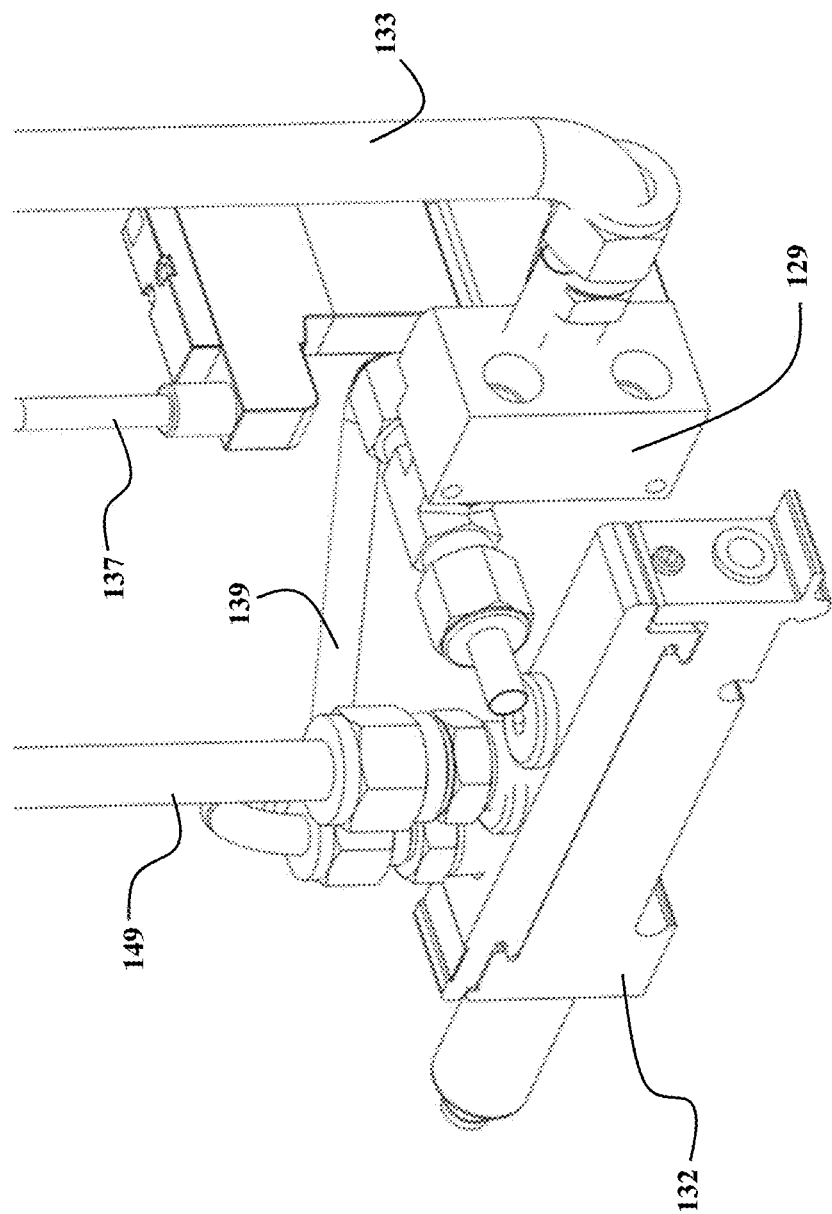
FIG. 9D is a detailed rear view of the vacuum module shown in FIGS. 9A-9C.

Vacuum generator 132, which is mounted on the robot's second arm 130 via a mounting plate 134, is in fluid communication with the cup 140 via conduit 149, shaft 147 and cup mount 146. The generator 132 is configured to reversibly supply sub-atmospheric pressure to the cup 140 in response to the opening and closing of a vacuum generator pneumatic control valve 135. As shown, the valve 135 is an electrical actuator, which configured to open or close pneumatic valve 135 in response to electrical signals from the electrical controller 280. In other embodiments, the valve may be opened by pneumatic or hydraulic forces, instead of by electrical actuation. When valve 135 opens, air pressure from the air pressure supply line 133 is permitted to pass through the valve 135, through conduit 139 (air pressure supply line to venturi), into the vacuum generator 132, and out the exhaust/muffler 132m. The flow of pressurized air through 139 and out the muffler creates a venturi effect, whereby subatmospheric pressure is produced in conduit 149. This subatmospheric pressure is communicated to the cup 140, such that when the cup 140 is pressed down against an egg to be relocated, and the subatmospheric pressure is applied, the egg is sealably held to the cup 140 by the negative pressure. Once the robot 101 moves the egg to a desired new location, an electrical signal carried along wire 137 causes the valve 135 to close, thereby releasing the temporary subatmospheric pressure, and releasing the egg. Connection point 136 facilitates routine valve 135 replacement by obviating the need to cut and splice wire 137. And as shown in FIG. 9D, an air valve base ported aluminum block 129 directs the airflow to the components, to and from valve 135.

Figure 9E:
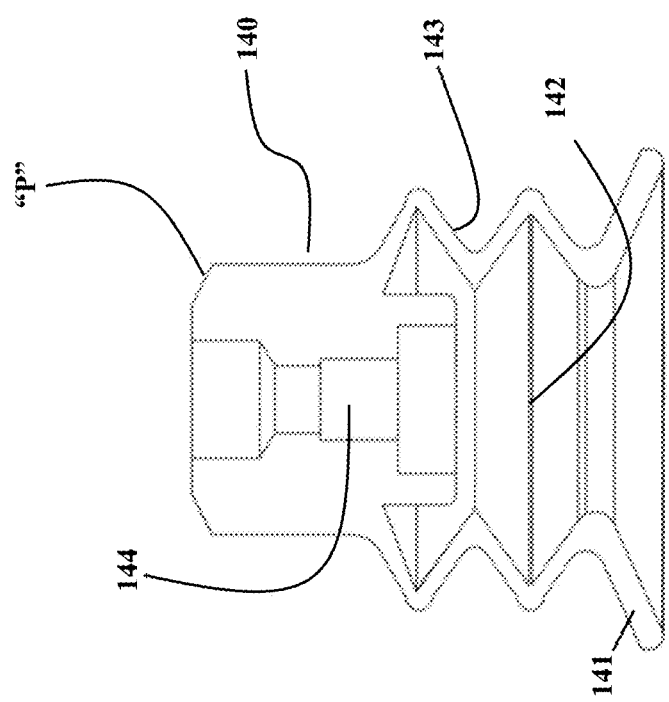
FIG. 9E is a detailed view of the flexible cup shown in FIG. 9A.

As shown in FIG. 9E, the flexible cup 140 comprises a mounting point "P", a vacuum passage 144, a soft lower lip 141, a filter screen 142, and a semi-rigid double below 143. The skilled person will appreciate that other suitable flexible suction cups may be used in the practice of this invention.

Figure 10:
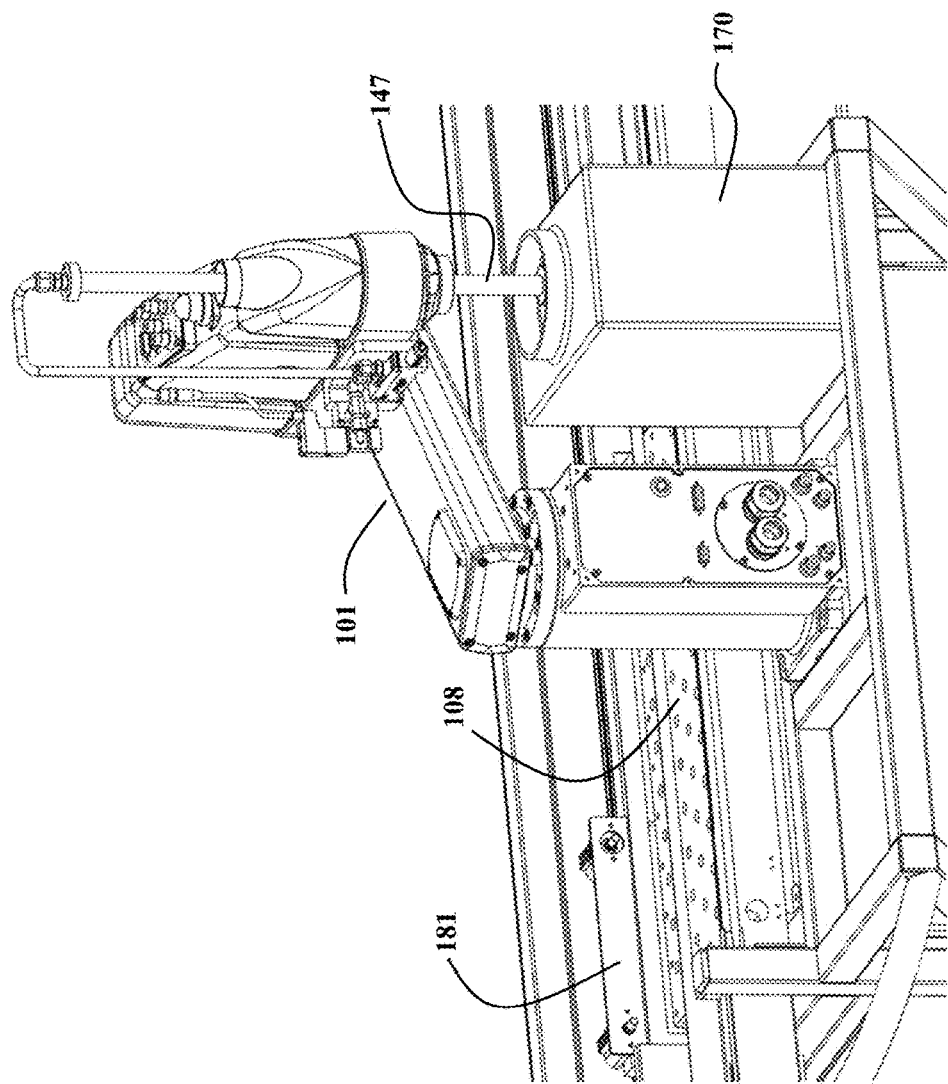
FIG. 10 illustrates the flexible vacuum cup of the egg relocation apparatus of FIG. 9A being immersed in a bath of cleaning/disinfection solution.

As shown in FIG. 10, the apparatus 10 may comprise a reservoir/tank 170 for holding a volume of cleaning/sanitizing solution. At user-selected or pre-programmed intervals, the robotic arm dips the shaft 147 and flexible cup 140 into the tank 170. Negative pressure is applied, by action of the pneumatic controller and the vacuum generator 132, to draw solution into the shaft 147 through the cup 140. Solution is then circulated throughout the shaft 147 and conduits for a period of time sufficient to sanitize/clean said shaft 147 and conduits.

The cycle of egg picking and relocating is repeated until each of the eggs to be relocated is removed from the tray 7 and placed into its desired location (e.g. egg carton, box, crate, tray, bin, and the like). Once the non-viable eggs are removed, the tray 7 containing only viable eggs is moved from the candling area 100 to the viable egg staging area 200. Here, empty spaces may be filled (or not) with viable eggs, either by hand or by another robotic arm.

Accordingly, in an embodiment, the egg picking and relocation cycle may be performed by the apparatus 10 according to the following steps:

1. Information describing the location of the non-viable eggs is acquired and stored;
2. Egg location information is communicated to the robot controller;
3. The robot controller determines what motions are required to bring the cup 140 into contact with the non-viable egg(s) to be relocated;
4. The robot controller instructs the robot 101 to move arm 120 about axis A2, arm 130 about axis A1, and shaft 147 vertically, to pick up a non-viable egg to be relocated;
5. Once the shaft 147 is moved sufficiently downward to cause the cup 140 to contact a non-viable egg to be relocated, the electrical controller 280 instructs the valve 135 to open, allowing pressurized air from conduit 133 to pass through valve 135, into conduit 139 and into vacuum generator 132;
6. Pressurized air passing through the vacuum generator 132 and out the muffler produces negative pressure in conduit 149, which produces subatmospheric pressure in the air between the cup 140 and the egg to be relocated, thereby temporarily holding the egg to the cup;
7. The robot controller instructs the robot 101 to move shaft 147 vertically, arm 120 about axis A2 and arm 130 about axis A1, to carry the egg to a new location;
8. The electrical controller 160 instructs the valve 135 to close, allowing the air between the cup 140 and the egg to return to atmospheric pressure, which allows the egg to be released from the cut 140;
9. The cycle is repeated until all non-viable eggs are removed from the tray and relocated.

The cup 140 may be cleaned at any time by moving the cup into the sanitization vessel 170 and passing air back and forth to cause sanitizer solution to cleanse the cup. The solution may also be drawn up into the shaft 147 and various conduits, to cleanse the shaft and conduits.

As described below, different egg remover "heads" may be mounted on the robot, in a modular fashion, to accommodate the needs of different hatcheries (e.g. to accommodate different types of egg trays).

Forty-Two-Egg Remover Head.

Figure 11:
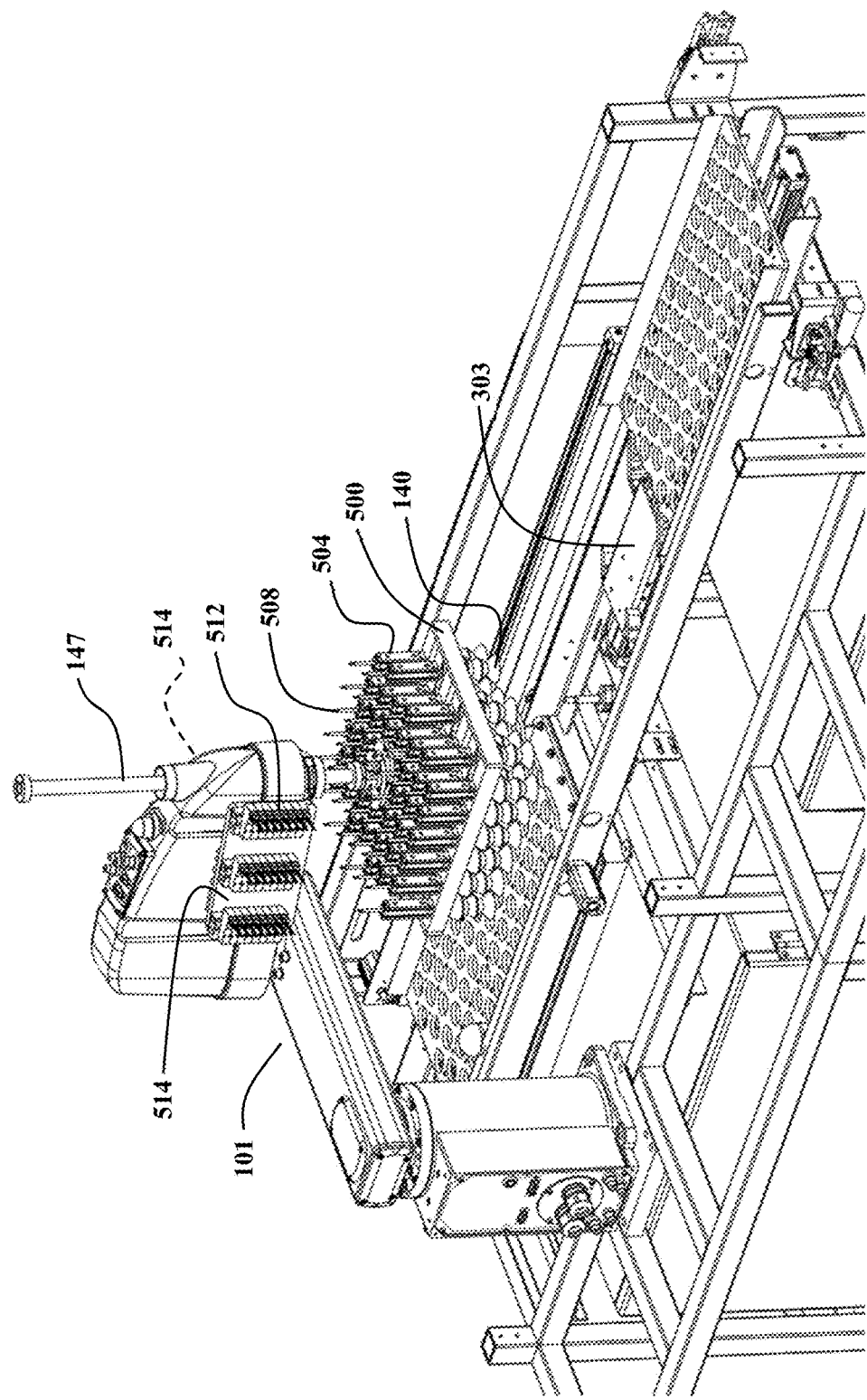
FIG. 11 shows an embodiment of the egg relocation apparatus wherein the robotic arm is mechanically connected to a plurality of flexible cups, each cup operably connected to its own vacuum generator and electrical and pneumatic circuitry. This version of the egg relocation apparatus is capable of removing and relocating multiple eggs at a time.
Figure 12:
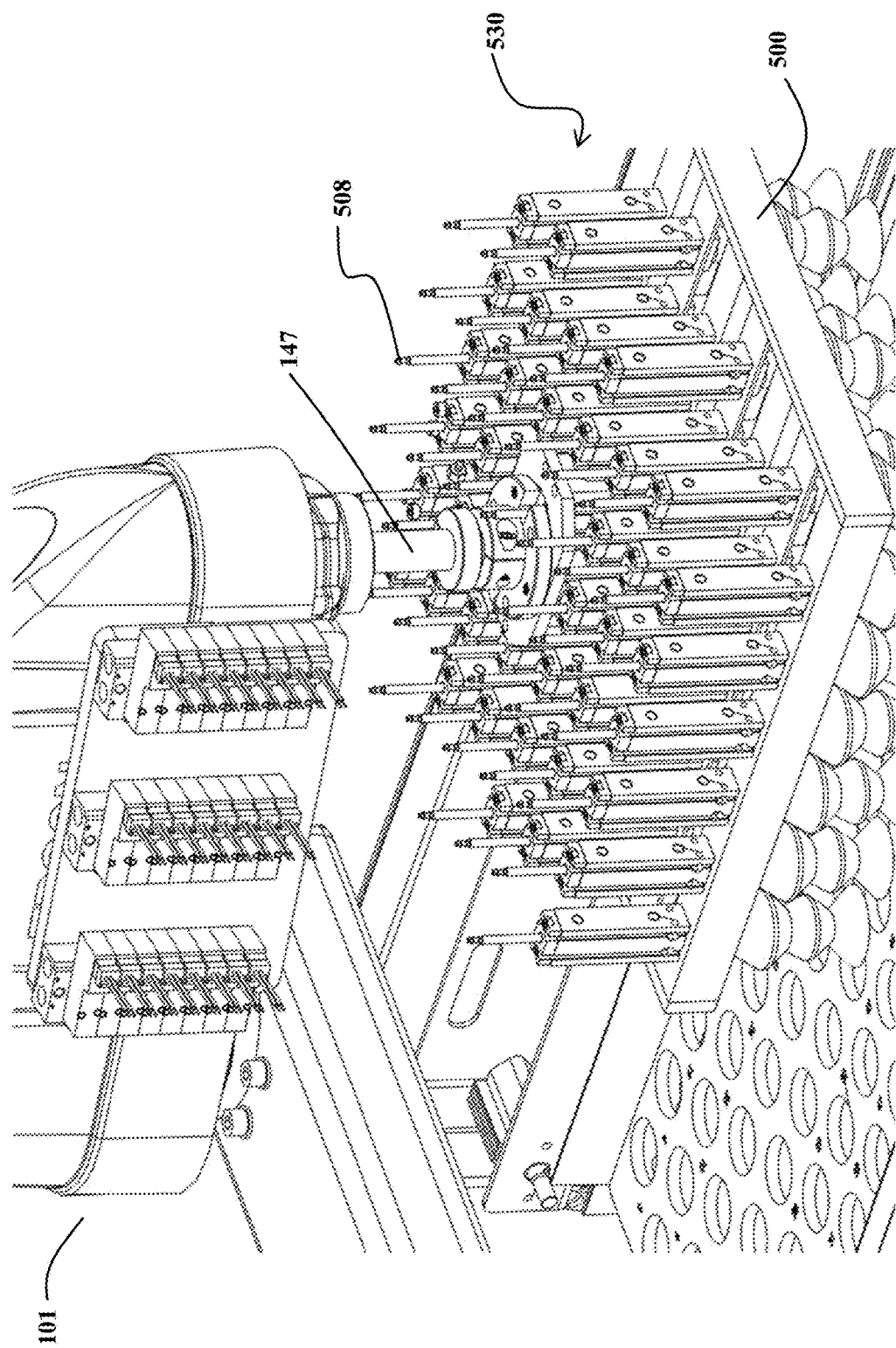
FIG. 12 is a magnified view of the array of vacuum generators and egg removers.
Figure 13:
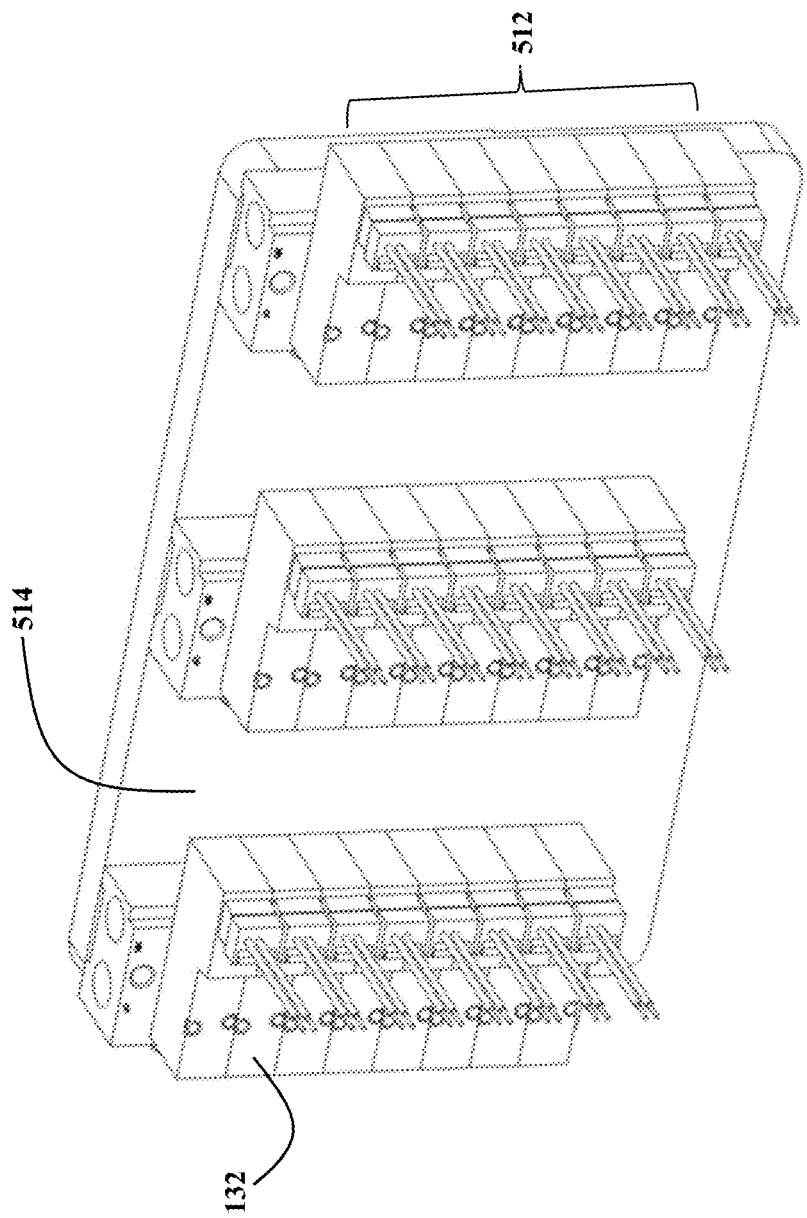
FIG. 13 is a magnified view of multiple vacuum generators mounted on a vacuum generator base.
Figure 14:
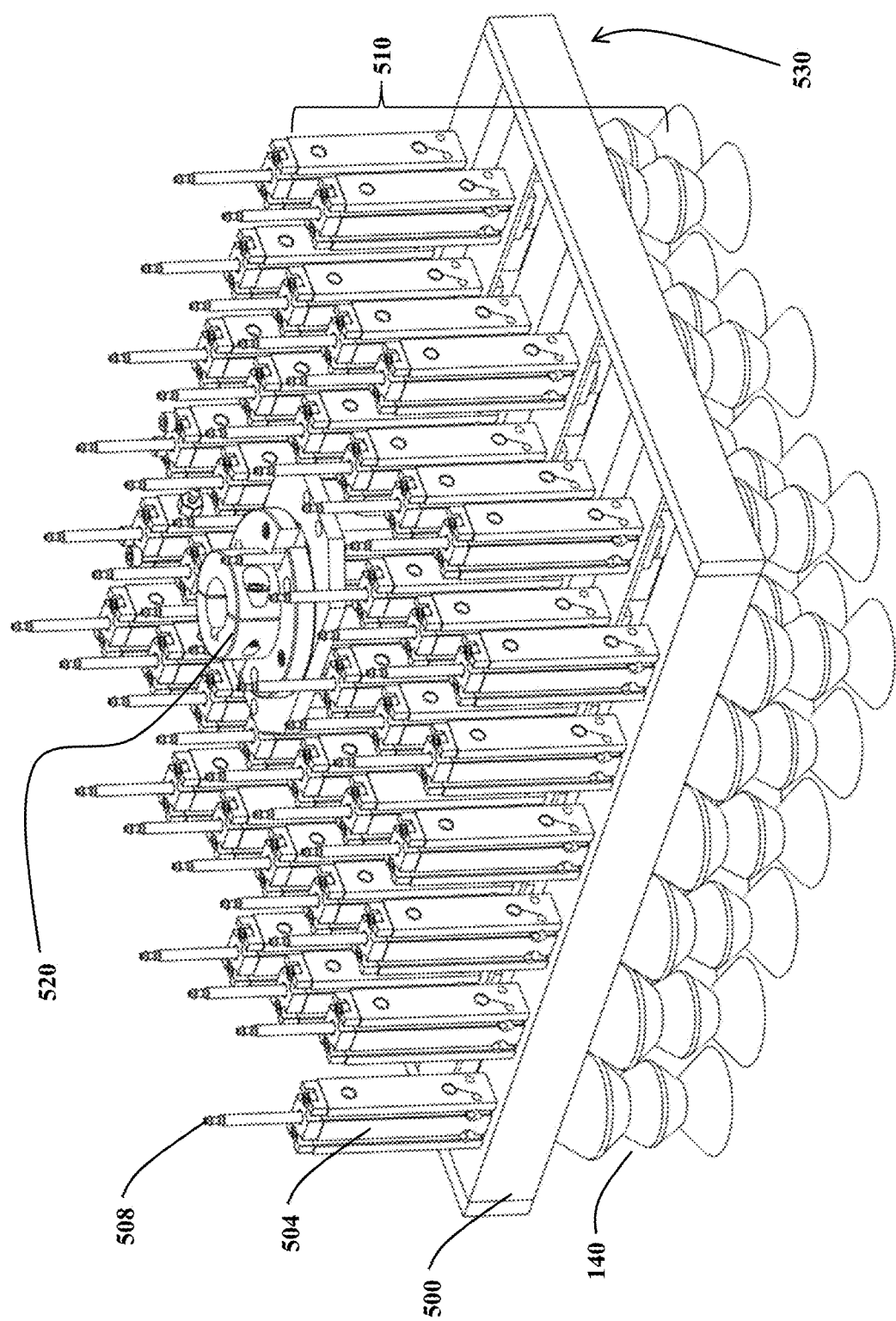
FIG. 14 is a magnified view of the forty-two (42) egg remover head 530.

As indicated in FIG. 11, the egg removal and relocation apparatus may comprise a robot 101 that is mechanically and operably connected to an array of suction cups 140. As shown, each suction cup 140 is mechanically connected to, and movable by, an independent actuator 504. Each actuator 504 is mounted to an egg remover base 500, which base is mounted on shaft 147 of robot 101. As shown in FIG. 14, shaft 147 may connect to the egg remover base 500 via shaft attachment means 520. The attachment means may be a segmented annual ring system, or any other mechanically suitable means for attaching the cylindrical shaft to the egg remover base 500. Each suction cup 140 is in fluid communication with an individual vacuum generator 132 via a conduit (not shown), which fluidly connects each suction cup 140 with its corresponding vacuum generator 132. Each conduit is sealably connectable to an airline receiver 508. Moreover, each actuator 504 is operably connected to the robot 101 (e.g. via electrical wires for electric actuators, or via air conduits for pneumatic actuators), such that each combination of suction cup 140 and actuator 504 (together referred to as "egg remover", or 510) is individually controllable to remove and relocate eggs. The independent actuator 504 provides an additional benefit, which is to reduce the risk of contamination and improve biosecurity (i.e. so that each suction cup 140 only comes into contact with the non-viable eggs). Furthermore, since each suction cup 140 has its own independently controllable vacuum generator 132, only the cups 140 that are picking out bad eggs generate vacuum, reducing the risk of cross-contamination. The vacuum generators 132 may be mounted as banks 512 (as shown), mounted to a vacuum generator bank base 514, which base may be mounted on the robot 101. As indicated by the dotted line, another base 514 (having banks of vacuum generators 132 mounted thereto) is present on the opposite side of the robot 101). Finally, the embodiment disclosed in FIGS. 11 to 14 is capable of removing and relocating from 0 to 42 eggs per move/cycle. Thus, the apparatus shown in FIGS. 11 to 14 comprises an array of 42 egg removers 510, and is capable of picking, removing and relocating 42 eggs (e.g. non-viable eggs) per move. Accordingly, this apparatus can process an eighty-four (84) egg flat in two moves. Although not shown (to simplify the drawings), the apparatus comprises suitable air conduits and/or electrical wires to connect the vacuum generators to the egg removers 510.

Six-Egg Remover Head.

Figure 15:
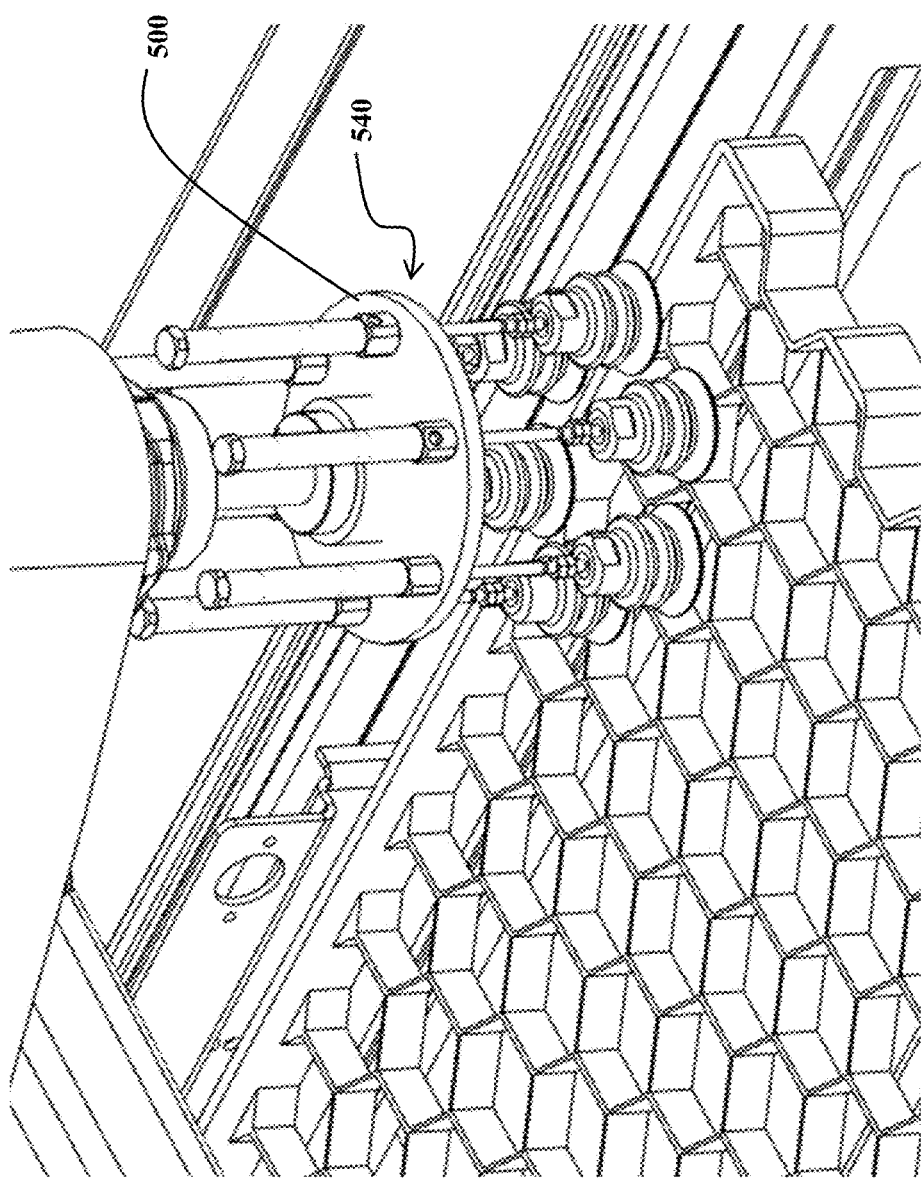
FIG. 15 is a view focusing on the six (6) egg remover head 540.

In another embodiment, the egg removing and relocation apparatus may be equipped with a six (6) egg per move egg remover head 540 (FIG. 15). Like the 42 egg remover head 530, each egg remover 510 is independently controllable, allowing the apparatus to remove and relocate 0 to 6 eggs per move/cycle.

Single-Egg Remover Head.

Figure 16:
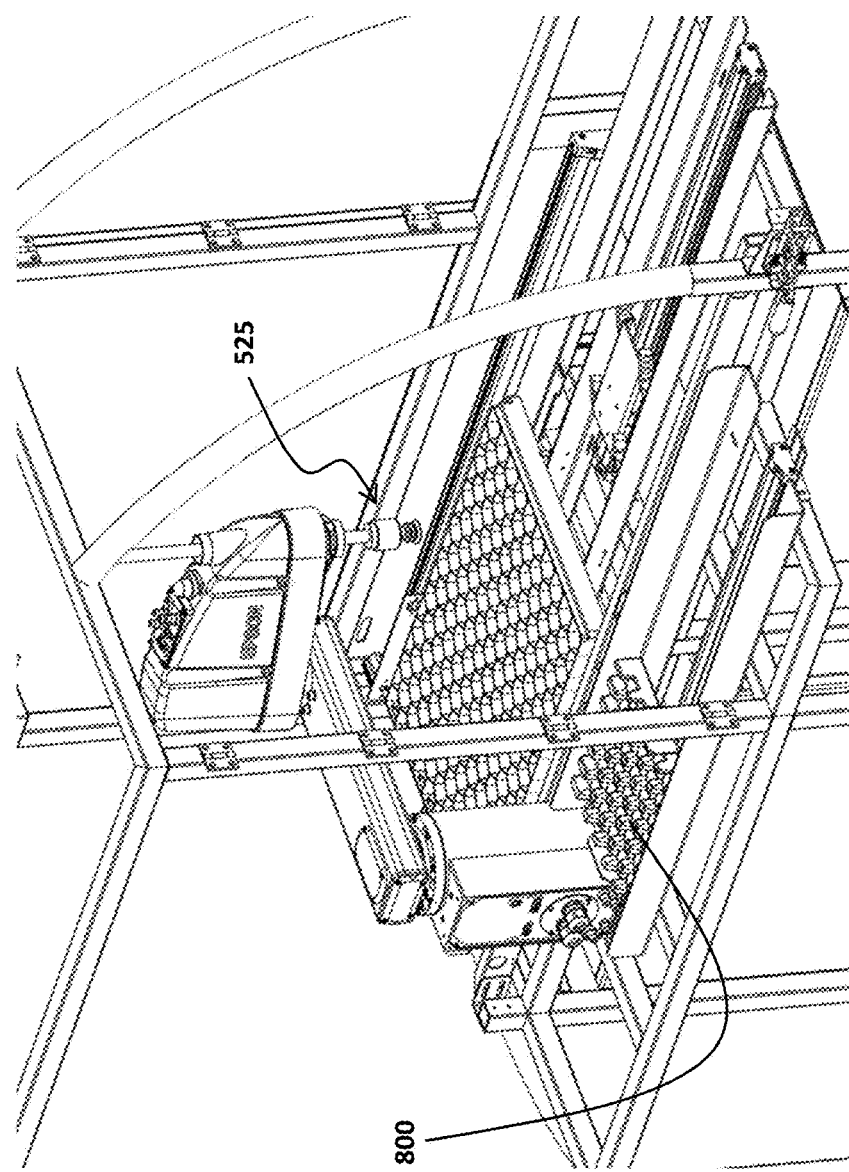
FIG. 16 shows an embodiment of the apparatus equipped with a single-egg remover head 525 and configured to accommodate wide format egg trays. An optional egg receiving tray 800 is also depicted.

In still another embodiment (FIG. 16), the apparatus may be equipped with a single-egg remover head 525, like the apparatus depicted in FIGS. 1 to 4, and be configured to accommodate wide-format trays (e.g. 150-egg trays). In this embodiment, cycle time is necessarily dependent upon the number of eggs that must be to be removed & relocated per cycle. However, this configuration offers several benefits including reduced manufacturing costs, reduced maintenance requirements and greater simplicity. And similar to the embodiment shown in FIGS. 1 to 4, the embodiment shown in FIG. 16 is capable of precisely repacking removed eggs. In such a case, a receiving tray 800 may be positioned such that the apparatus is capable of filling the receiving tray with the removed eggs. When the receiving tray is full of removed eggs (e.g. non-viable eggs), the apparatus expels the filled receiving tray, so that an empty receiving tray 800 may be placed into the receiving position, thus allowing the repacking process to continue.

Advantageously, each egg remover head (e.g. single-egg, six-egg, forty-two-egg, etc.) may be used with any egg flat configuration, based upon each hatchery's needs.

Now that the invention has been disclosed, Applicants envision many mechanically reasonable configurations for the various components of the apparatus.

The invention will now be described by the following set of non-limiting claims.

What is claimed:

1. An egg candling and relocation apparatus, comprising:
   a. a user interface;
   b. an entrance, an egg candling area, an egg staging area and an exit;
   c. supports configured to receive and permit the conveyance of a tray holding a plurality of eggs;
   d. one or more conveying means, for conveying the trays from the entrance, to the candling area, to the egg staging area, and to the exit;
   e. an egg candling energy means, for directing energy at the plurality of eggs;
   f. an energy detection means, for detecting the energy that passes through the plurality of eggs and for converting the detected energy into a signal;
   g. a signal processing means, for converting the signal into at least one status signal of one or more eggs;
   h. a robot, comprising a working arm equipped with one or more flexible cups, for picking up and relocating eggs based upon the status of said eggs, wherein the robot is mounted onto the apparatus such that a range of motion of said robot permits said working arm and said one or more flexible cups to pick up any of the plurality of eggs while the tray is in the candling area; and
   i. a robot controller, an electrical controller, and a pneumatic controller, wherein each controller is electrically connected to the user interface;
   j. a four finger pusher, comprising four fingers that is configured to slide beneath the tray and engage with the tray to move the tray laterally, toward the exit, wherein when the four finger pusher slides beneath the tray, the four fingers flexibly and pivotably retract, and after a first set of two fingers clears the edge of the tray, said first set of two fingers pivot up to their resting positions, and wherein after the first set of two fingers return to their resting positions, the four finger pusher reverses direction, engages the first set of two fingers with the tray, thereby moving the tray from the egg staging area to the exit; and
   wherein the apparatus is optionally equipped with a single-, 6-, or 42-egg remover head.

2. The apparatus of claim 1, wherein the energy is visible light and the detection means is a camera.

3. The apparatus of claim 1, wherein the energy is sound waves and the detection means is a sound sensor.

4. The apparatus of claim 1, wherein the energy is infrared light and the detection means is a camera capable of detecting infrared light.

5. The apparatus of claim 1, wherein the energy is electromagnetic radiation and the detection means is a sensor capable of detecting the electromagnetic radiation.

6. A method for candling, removing and relocating eggs using the apparatus of claim 1, comprising the steps of:
   a. selecting an egg status that qualifies an egg for removal and relocation;
   b. loading a tray containing a plurality of eggs to be candled into the apparatus;
   c. moving the tray into the egg candling area;
   d. directing candling energy at the eggs;
   e. detecting energy that passes through the eggs;
   f. processing the detected energy into a status signal;
   g. transmitting the status signal to the robot controller;
   h. moving the robot's one or more flexible cups into contact with each egg having the selected egg status;
   i. applying subatmospheric pressure such that the one or more flexible cups and the eggs having the selected egg status become reversibly coupled to one another;
   j. moving the eggs having the selected egg status to a relocation area;
   k. restoring atmospheric pressure, to release the eggs having the selected egg status from the one or more flexible cups;
   l. repeating the process of picking up and relocating eggs until all eggs having the selected egg status have been relocated;
   m. moving the tray, now lacking the eggs having the selected egg status, to the egg staging area, wherein the steps of moving the tray is accomplished by pneumatic actuators, which are configured to grip and release the tray in response to appropriate pneumatic and/or electrical signals, and which are operably connected to a pneumatic cylinder, which is configured to move the actuators laterally, between the candling area and the egg staging area; and
   n. moving the tray from the egg staging area to the exit, wherein the four finger pusher slides beneath the tray and engages with the tray to move the tray laterally, toward the exit.

7. The method of claim 6, further comprising the step of handing the tray off to a downstream in ovo injection machine, which is reversibly tethered to the apparatus.

8. The method of claim 6, wherein when the four finger pusher slides beneath the tray, the four fingers flexibly and pivotably retract, and after a first set of two fingers clears the edge of the tray, said first set of two fingers pivot up to their resting positions.

9. The method of claim 8, wherein after the first set of two fingers return to their resting positions, the four finger pusher reverses direction, engages the first set of two fingers with the tray, and thereby moves the tray from the egg staging area to the exit.

10. The method of claim 9, wherein once the four finger pusher reaches its distal most range of motion with respect to the anterior end of the apparatus, the four finger pusher reverses direction and moves until a second set of two fingers clear the tray.

11. The method of claim 10, wherein once the second set of two fingers clear the tray, the four finger pusher reverses direction, engages the second set of fingers with the tray, and moves the tray through the exit.

12. The method of claim 11, further comprising the step of handing the tray off to a downstream in ovo injection apparatus.

\* \* \* \* \*